(12) United States Patent
Graham et al.

(10) Patent No.: US 6,259,242 B1
(45) Date of Patent: Jul. 10, 2001

(54) APPARATUS INCORPORATING A SENSING CONDUIT IN CONDUCTIVE MATERIAL AND METHOD OF USE THEREOF FOR SENSING AND CHARACTERIZING PARTICLES

(75) Inventors: Marshall D. Graham, Nicholasville, KY (US); Harvey J. Dunstan, Herts (GB)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/320,496

(22) Filed: May 26, 1999

(51) Int. Cl.[7] .............................. G01N 15/12; G01N 27/08
(52) U.S. Cl. ...................... 324/71.4; 324/439; 324/446; 377/12
(58) Field of Search ...................................... 324/439, 444, 324/446, 450, 71.4, 71.1; 73/61.71; 377/12

(56) References Cited

U.S. PATENT DOCUMENTS

| 2,656,508 | 10/1953 | Coulter . |
| 2,869,078 | 1/1959 | Coulter et al. . |
| 2,985,830 | 5/1961 | Coulter et al. . |
| 3,259,842 | 7/1966 | Coulter et al. . |
| 3,502,974 | 3/1970 | Coulter et al. . |
| 3,771,058 | 11/1973 | Hogg . |
| 3,810,010 | 5/1974 | Thom . |
| 3,902,115 | 8/1975 | Hogg et al. . |
| 3,949,198 | 4/1976 | Coulter et al. . |
| 4,161,690 | 7/1979 | Feier . |
| 4,284,496 | * 8/1981 | Newton ........................ 324/71.4 X |
| 4,438,390 | * 3/1984 | Hogg ............................ 324/71.1 |
| 4,797,624 | 1/1989 | Dunstan et al. . |
| 6,111,398 | * 8/2000 | Graham ........................ 324/71.4 |

* cited by examiner

Primary Examiner—Glenn W. Brown
(74) Attorney, Agent, or Firm—Warren W. Kurz; Mitchell E. Alter

(57) ABSTRACT

Apparatus for sensing and characterizing particles suspended in a liquid medium includes a particle-sensing structure having a continuous wall defining a hydrodynamically smooth conduit through which the liquid suspension of particles is caused to pass simultaneously with an electrical current. Particles passing through the conduit are sensed and characterized by monitoring changes in the electrical current through the conduit. According to the invention, the continuous, conduit-defining wall is made entirely of a material having an electrical resistivity less than or equal to that of the liquid medium. Thus, the apparatus of the invention is similar to the conventional Coulter aperture (conduit) except that the aperture is formed from an electrically conductive material instead of a dielectric material.

20 Claims, 8 Drawing Sheets

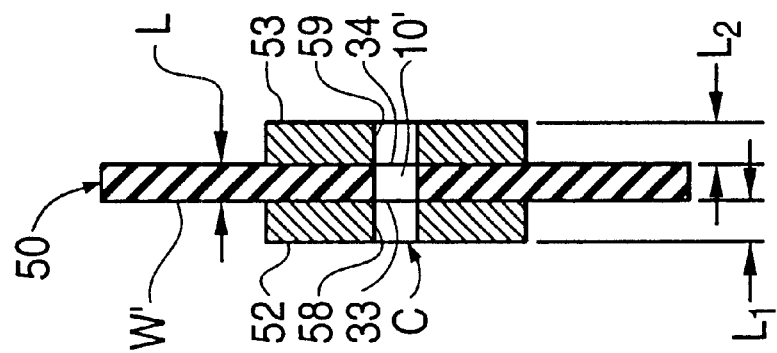
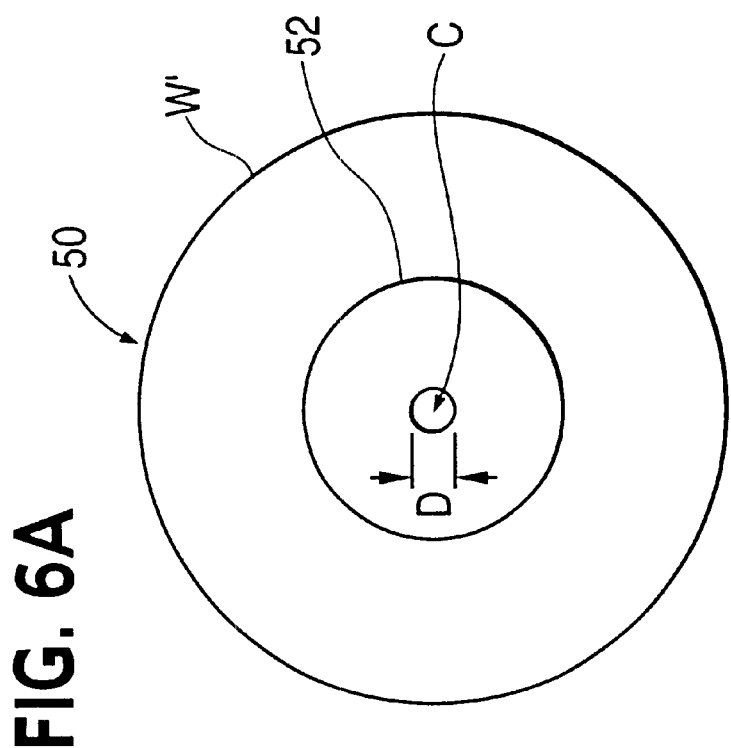
FIG. 6A
FIG. 6B

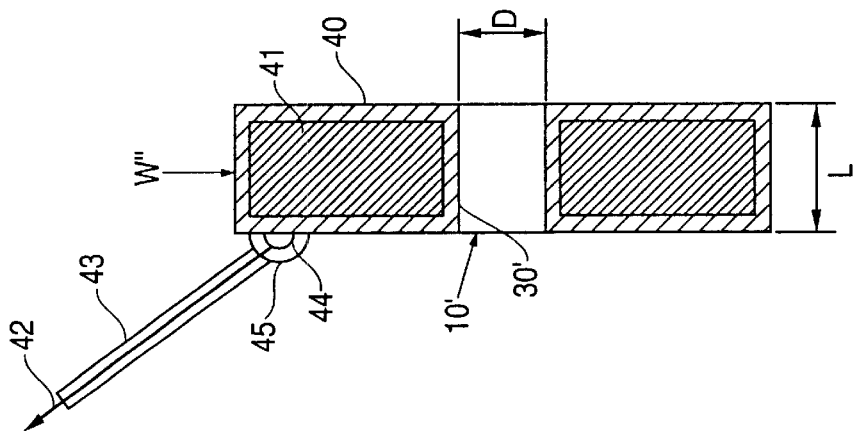
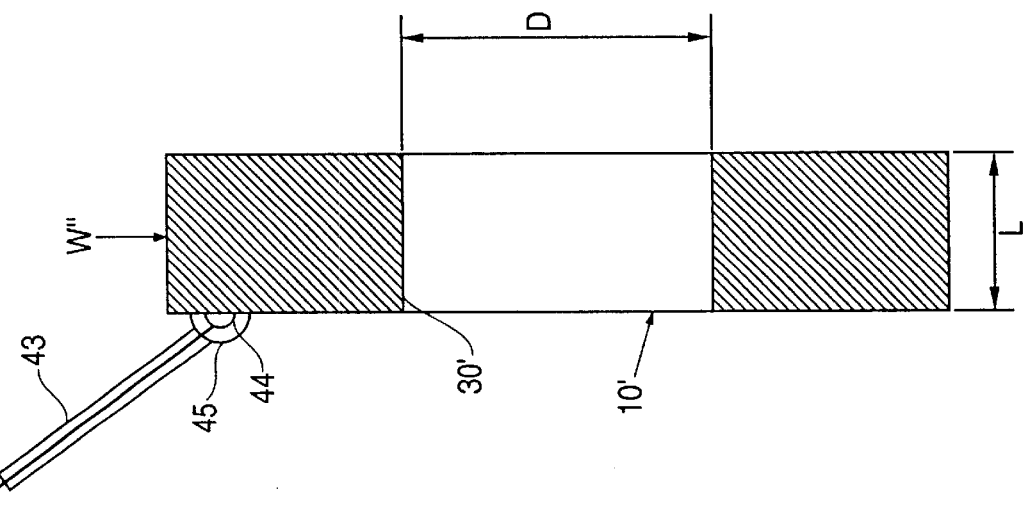

US 6,259,242 B1

APPARATUS INCORPORATING A SENSING CONDUIT IN CONDUCTIVE MATERIAL AND METHOD OF USE THEREOF FOR SENSING AND CHARACTERIZING PARTICLES

CROSS-REFERENCE TO RELATED APPLICATIONS

This application is related to application U.S. patent application Ser. No. 08/887,588, filed Jul. 3, 1997 and entitled "Method and Apparatus for Sensing and Characterizing Particles" (now issued as U.S. Pat. No. 6,111,398). This application is also related to a Continuation-In-Part of said application, filed Jul. 1, 1998 as U.S. patent application Ser. No. 09/108,997 and entitled "Potential-Sensing Method and Apparatus for Sensing and Characterizing Particles by the Coulter Principle". Both related applications are incorporated herein by reference, being assigned in common with this application to the same assignee.

CROSS-REFERENCE TO RELATED PATENTS

Reference is made to the following U.S. patents, each owned by the assignee of the present invention: U.S. Pat. Nos. 2,656,508; 2,869,078; 2,985,830; 3,259,842; 3,502,974; 3,771,058; 3,810,010; 3,902,115; 3,949,198; and 4,797,624. The disclosures of these patents provide exemplary prior art of interest regarding the invention hereinafter described, each of said patents being incorporated herein by reference.

Reference is also made to U.S. Pat. No. 4,161,690. The disclosure of this patent provides a further example of the prior art related to the invention hereinafter described and is incorporated herein by reference.

BACKGROUND OF THE INVENTION

1. Field of the Invention

The present invention relates to improvements in methods and apparatus for sensing and characterizing small particles, such as blood cells or metallic powders, suspended in a liquid medium having electrical impedance per unit volume which differs from that of the particles. More particularly, one aspect of the invention relates to improvements in methods and apparatus for sensing and characterizing such particles, whereby increased sensitivity to particle characteristics other than physical volume is provided. A second aspect of the invention relates to improvements in the non-volumetric sensitivity of methods and apparatus for sensing and characterizing such particles by apparatus operating according to the Coulter principle.

2. Discussion of the Prior Art:

U.S. Pat. No. 2,656,508 to Wallace H. Coulter (the '508 patent) discloses a seminal method for sensing particles suspended in a liquid medium. An exemplary apparatus for implementing such method is schematically illustrated in FIG. 1. Such apparatus comprises a dual-compartment dielectric vessel 6, which defines first and second compartments 6A and 6B separated by a dielectric wall 7. Each of the compartments 6A and 6B is adapted to contain, and is filled with, a liquid medium M. Wall 7 is provided with a relatively large opening 7A, which is sealed by a thin wafer W made of a homogeneous dielectric material. A small through-hole formed in wafer W provides a conduit 10, which constitutes the only operative connection between compartments 6A and 6B. The particles to be sensed and characterized are suspended at an appropriate concentration in liquid medium M and introduced into compartment 6A through a suitable inlet port 8 (or 9) formed therein. A vacuum, provided by an appropriate source in liquid-handling system 13 and operatively coupled to an outlet port 11 suitably formed in compartment 6B, causes the particle suspension to flow from compartment 6A into compartment 6B through conduit 10, discussed in detail below. Each particle in the suspension displaces its own volume of liquid medium M, and conduit 10 provides a consistent reference volume against which that displaced volume may be compared. If the dimensions of conduit 10 and the concentration of particles in the suspension are appropriately selected, particles can be made to transit conduit 10 more or less individually. Conduit 10 then functions as a miniature volumeter, capable under suitable conditions of making sensible the liquid displaced by individual microscopic particles.

To enable convenient sensing of the liquid displacement occasioned by particles transiting conduit 10, liquid medium M is made to have electrical impedance per unit volume which differs from that of the particles. Both aqueous and non-aqueous liquid solutions of a variety of electrolytes have been used as medium M to suspend and carry the particles being characterized through conduit 10. The electrical resistivity p of such liquid media is usually in the approximate range between 30 ohm·cm and 200 ohm·cm; e.g., at room temperature the resistivity of a commercial isotonic saline solution (Isoton II, Coulter Corporation) is approximately 61.4 ohm·cm. The contrast in electrical impedance between particle and medium M thus converts the volume of displaced liquid into a proportional change in the electrical impedance of the liquid column in conduit 10.

The remainder of the apparatus in FIG. 1 forms a two-electrode measurement system responsive to such changes in electrical impedance. Excitation electrodes 15 and 16 are positioned in respective compartments 6A and 6B and operatively connected to a source 17 of electrical current, whereby a nominal electrical current is caused to flow through conduit 10 simultaneously with the particle suspension. Sensing circuitry 18, also operatively connected to excitation electrodes 15 and 16, operates to sense and process pulsations in current between these electrodes. Thus, as individual particles pass through conduit 10, sensing circuit 19 produces an electrical signal pulse having an amplitude which is proportional to the impedance change and therefore characteristic of the particle volume. Additional circuits 20 process the particle signal pulses to provide a count of particles exceeding some particular volumetric threshold. If current source 17 is caused to provide a constant current (so that pulse amplitudes are made insensitive to temperature-induced changes in the electrical conductivity of suspending medium M), the volumetric distribution of the particles may be conveniently characterized through use of multiple-threshold circuitry 21 as described in U.S. Pat. No. 3,259,842 to Wallace H. Coulter et al. Further, if current source 17 is caused to provide at least one alternating-current component at high frequency as discussed in U.S. Pat. No. 3,502,974 to Wallace H. Coulter and W. R. Hogg, an apparent volume reflecting the internal conductivity of biological cells may be similarly characterized. If liquid-handling system 13 comprises a positive-displacement metering system, e.g., such as disclosed in U.S. Pat. No. 2,869,078 to Wallace H. Coulter and Joseph R. Coulter, Jr., such particle counts may be readily displayed or recorded in terms of particle concentration by appropriate devices 22. This method of sensing and characterizing particles, by suspending them in a liquid medium having electrical impedance per unit volume which differs from that of the particles and passing the resulting particle suspension through a constricting conduit while monitoring the electrical current flow through the conduit, has become known as the Coulter principle.

A substantial interphase layer of anions or cations may result when metallic conductors are immersed in a liquid medium comprising ionic species and the ionic medium is constrained to maintain a potential gradient in the vicinity of the conductive material. The predominant ionic type surrounding such conductors depends on the polarity of the potential gradient at the material surface, i.e., on whether electrons enter or leave the material. As noted in the '508 patent, excitation electrodes 15 and 16 develop such concentration polarization layers at their surfaces. At a given temperature, properties of said polarization layers depend on the material of each electrode, the electrolyte, and the local rate of electron exchange (i.e., the current density) through the polarization layer. In the electrode art it is known to minimize local gradients in current density, whereby polarization layers are substantially uniform in thickness and vary from approximately an ionic diameter at very low current densities to perhaps $3 \times 10^{-5}$ mm at high current densities. If a given current density is to be maintained between said electrodes, the electrode potentials must be increased to overcome the resistance to electron transfer represented by the polarization layers, and the ions must migrate into medium M. The consequent potential differentials across the thicknesses of the polarization layers are manifested as an overvoltage above the reversible potential at the surface of each electron-exchanging electrode. Thus, the polarization layers act as capacitances in parallel with the charge-transfer resistances, the overvoltages being a logarithmic function of the current density through the two layers. If the potential of electrode 15 or 16 is made to exceed the reversible potential of the particular electrode material in the particular medium M, electrolysis occurs and the consequent bubbles interfere with the ability to sense particles transiting conduit 10.

Electrodes made from metals in the platinum group have comparatively stable overvoltages, and the effects of electrode electrochemistry are further minimized in Coulter apparatus by locating large-area platinum electrodes 15 and 16 away from conduit 10, sometimes in separate electrode chambers electrolytically connected to compartments 6A and 6B. Even so, the electrochemical processes contribute series impedance components and effective back-sources to the electrical equivalent circuit constituted by the electrolytic path between said electrodes and through conduit 10. Consequently, the impedance change occasioned by a particle transiting conduit 10 is superimposed on impedance components originating in the portions of medium M in compartments 6A and 6B. Thus, sensing circuit 19 is preferably AC-coupled with a suitable transient response, whereby the relatively slow impedance variations related to electrochemistry at electrodes 15 and 16 are prevented from interfering with particle-related impedance changes responsible for the desired signal pulses.

Outside the polarization layers ions migrate by a combination of diffusion and ionic drift due to the electric field established between electrodes 15 and 16 by current source 17. Ions migrate through medium M in compartment into the hydrodynamic flow pattern and are carried through Coulter conduit 10 by convective flow. The effective current in the vicinity of conduit 10 is ohmic as determined by the electrical resistivity p of medium M, and the local current density is determined by the geometry along the path of ionic drift. The result is a low resistance due to the portions of medium M in the two compartments of vessel 6, in series with the high resistance formed by the liquid column in conduit 10. Excitation current from current source 17 is limited to the value that causes Joule boiling in conduit 10.

Central to the Coulter principle is volumeter conduit 10, which enables electrical sensing of particle volume by constricting the electric field established in liquid medium M filling vessel 6. Any second path of current conduction between compartments 6A and 6B would act in parallel with the current path through the liquid column in conduit 10 and so by shunting effects would act to decrease the amplitude of signal pulses. For example, if wall 7 or wafer W were to be made of a material less resistive than medium M, intuition suggests that the liquid column in conduit 10 would be bypassed due to its higher resistivity, with excitation current flowing through the more conductive material in proportion to its greater conductivity and area. Consequently, in all Coulter apparatus, functional conduit 10 is formed in a homogeneous dielectric material, the electrical resistivity of which is typically at least $10^9$ times that of suspending medium M. In the '508 patent the conduit is a pinpoint aperture formed directly in the wall of a glass vessel, but such conduits proved both difficult to reproduce to the desired precision and prone to damage. An early alternative utilized a separate wafer W, cut from glass capillary tubing and sealed over opening 7A in wall 7 so that the tubing conduit formed conduit 10, but conduit geometry of such wafers was unstable under the glass-fusing methods required for reliable seals. Due to excellent mechanical and dielectric properties, precision ring jewels made of ruby or sapphire are recommended as conduit wafers W in U.S. Pat. No. 2,985,830 to Wallace H. Coulter et al., and such "Coulter wafers" or "aperture wafers" are now extensively used to provide conduit 10. Critical applications may benefit from the superior thermal conductivity of dielectrics such as beryllium oxide or diamond (U.S. Pat. No. 3,771,058 to W. R. Hogg).

A traditional Coulter volumeter conduit 10 (also referred to as a "Coulter aperture") comprises a continuous surface or wall 30 of length L which defines a right cylindrical opening of circular cross-section and diameter D through a homogeneous dielectric wafer W of thickness L and electrical resistivity greater than $10^{12}$ ohm·cm. As a result, conduit wall 30 surrounding the flows of suspension and excitation current through conduit 10 comprises a single substantially axisymmetric, delimited region of uniformly high resistivity in any longitudinal conduit section. Due to the high resistivity of Coulter wafer W, there is no significant electrical interaction between the material comprised in the wafer and liquid medium M. Consequently, functional attributes of the FIG. 1 apparatus are substantially independent of the specific dielectric material used to form a functional Coulter wafer and the particular medium M used to carry particles through Coulter conduit 10 therein.

Characteristics of signal pulses generated by particles transiting conduit 10 result from complex particle interactions with both the electric field established in liquid medium M by the excitation current and the hydrodynamic field established by the suspending medium carrying the particles through the conduit. For a given particle trajectory through conduit 10, pulse amplitude depends linearly on particle volume and excitation current, but both conduit fields are nonhomogeneous and trajectory-dependent artifactual pulses may be generated. As reviewed in cross-referenced U.S. patent application Ser. No. 08/887,588, considerable remedial art has been developed which minimizes the effects of artifactual pulses on volumetric distributions. Distributional artifacts due to near-wall particle trajectories may be eliminated by causing fluid-handling system 13 to appropriately inject particle suspension through flow director 9 in FIG. 1 (e.g., as described in U.S. Pat. No. 3,810,010 to R. Thom) or reduced by pulse-edit circuit 23 (e.g., as disclosed in U.S. Pat. No. 4,797,624 to H. J. Dunstan et al.). Similar artifacts due to particles on recursing trajectories at the exit of conduit 10 may be eliminated by causing fluid-handling system 13 to provide particle-free sweep-flow via inlet 12 in compartment 6B (e.g., as disclosed in U.S. Pat. No. 3,902,115 to W. R. Hogg et al.) or reduced by pulse-edit circuit 24 (responsive, e.g., to an auxiliary signal as described in U.S. Pat. No. 4,161,690 to M. Feier). Volumetric effects of particle coincidence within conduit 10 may also be limited by correction circuit 25 (e.g., as described in U.S. Pat. No. 3,949,198 to Wallace H. Coulter and W. R. Hogg). When appropriately provided with such facilitating art, Coulter apparatus can generate nearly ideal volumetric distributions for particles transiting conduit 10.

Coulter conduits having diameters ranging between approximately 0.015 mm and 0.200 mm, with conduit length-to-diameter ratios L/D between 0.75 and 1.2, have proven useful for a great variety of particles. For $\rho$ in ohm·cm and conduit dimensions expressed in $10^{-3}$ mm, the resistance of the liquid column within such conduits 10 may be estimated as the product of $\rho$ and the ratio of the length L to the cylindrical cross-sectional area $\pi D^2/4$, $$R_g = (4\rho \times 10^4)(L/\pi D^2) \text{ ohms.} \qquad \text{Eq. 1.}$$

Practically, resistances measured between electrodes 15 and 16 are significantly greater than the value calculated by Eq. 1. This is due primarily to effects of the well-known convex equipotentials extending outward from the orifices of conduit 10 and secondarily to the overvoltages of the polarization layers, about 1.1 volts for paired platinum electrodes. The contributions of the two inhomogeneous orifice fields may be approximated by adding a virtual cylinder of diameter D and length 0.2687D to Coulter conduit 10 at both conduit orifices. If this is done and the overvoltages are subtracted, calculated values based on the equivalent uniform cylindrical resistance correspond to measurements of voltage V (in volts) and current I (in amps) made between electrodes 15 and 16:

$$R_c = (V-1.1)/I = (4\rho \times 10^4)(L+0.5374D)/\pi D^2 \text{ ohms.} \qquad \text{Eq. 2.}$$

In principle, the expected change in resistance $\Delta R_c$ between electrodes 15 and 16 due to the passage of a particle through conduit 10 may be similarly estimated according to the resistivity contrast between the particle and the liquid medium M it displaces. Thus, for a dielectric cylindrical particle of length a and diameter d, Eq. 1 predicts a resistance change of $$\Delta R_c \approx (4 \times 10^4)(\rho_p - \rho)(a/\pi d^2) \text{ ohms,} \qquad \text{Eq. 3.}$$

where $\rho_p$ is the resistivity of the particle in ohm·cm and the particle dimensions (a, d) are in $10^{-3}$ mm. For dielectric particles, observed resistance changes are of the order of a few parts per hundred thousand of total resistance. The amplitude of the consequent signal pulse is proportional to the product of $\Delta R_c$ and the current I supplied by current source 17. Thus, signal-pulse amplitude should depend on the resistivity contrast $(\rho_p - \rho)$ and be of a polarity determined by whether the particle is of a dielectric material $(\rho_p > \rho)$ or a conductive material $(\rho_p < \rho)$.

However, particles formed of a conductive material also exhibit interphase effects if constrained to maintain a surrounding potential gradient in an electrolyte and so may exhibit a polarization layer and an overvoltage that acts to inhibit charge transfer at the particle surface. Unless the potential gradient represented by the ratio of the overvoltage to the thickness of the polarization layer is exceeded by the axial field gradient in conduit 10, particles of conductive materials are substantially insulated by the polarization layer and behave as though made of dielectric material. These effects are minimized in Coulter apparatus, and it is well known that under typical measurement protocols such apparatus yields positive pulsations substantially identical in amplitude for iso-volumetric spherical particles, irrespective of the electrical resistivity $\rho_p$ of the material forming the specific particle transiting conduit 10. Consequently, Coulter apparatus produces substantially equivalent volumetric distributions for such particles formed of a dielectric material and of a conductive material, and if the two types of particles were admixed and the mixture characterized, a third substantially equivalent volumetric distribution would be produced.

As has been noted, according to aforesaid U.S. Pat. No. 3,502,974 current source 17 is caused to provide a least one alternating-current component at high frequency. For such alternating currents in the range between 20 MHz and 25 MHz the insulating layer formed by a cell membrane is penetrated, and an apparent volume reflecting the internal conductivity of blood cells may be determined. The method is widely used in medical applications of Coulter apparatus and provides significant information that is otherwise unobtainable. At the aforesaid frequencies effects of the polarization layer surrounding conductive particles would be negated, and in principle this method should be applicable to non-biologic particles having significant conductivity. However, displacement currents through the body of the functional Coulter wafer W act to decrease pulse amplitudes, and skin effects further complicate the design of stable implementations. Practically, such instrumentation is complex, and reliable operation at such frequencies is difficult to achieve, particularly for conduit diameters larger than approximately 0.050 mm. The potential demand represented by such material-science applications has not justified commercial instrumentation comprising this complex and costly technology.

It is desirable that simple apparatus for sensing and characterizing particles be provided which offers increased sensitivity to particle characteristics other than physical volume.

SUMMARY OF THE INVENTION

In view of the foregoing discussion, an important object of this invention is to provide a novel apparatus of the type discussed above for sensing and characterizing particles, said apparatus offering increased sensitivity to particle characteristics other than physical volume.

Another object of the invention is to provide a particle-sensing structure that, owing to its unique constitution, provides a non-volumetric sensitivity in instruments of the type which sense and characterize particles by the Coulter principle.

In accordance with one aspect of the present invention there is provided a new and improved apparatus for sensing and characterizing particles suspended in a liquid particle-suspending medium to form a liquid suspension of particles. As in the prior Coulter art, the apparatus of the invention comprises:

(a) a particle-sensing structure defining a hydrodynamically smooth conduit through which a liquid suspension of particles to be sensed and characterized can be made to pass;

(b) a liquid handling-system for causing said liquid suspension of particles to pass through said conduit;

(c) a first electrical circuit for producing a nominal electrical excitation current through said conduit, said excitation current being effective to establish in the vicinity of said conduit an electric field providing a particle-sensitive zone in which changes in said nominal electrical excitation current, as produced by particles passing through said conduit simultaneously with said nominal current, are measurable; and (d) at least one second electrical circuit for monitoring a characteristic of the nominal electrical excitation current through the conduit to sense characteristics of particles passing through said conduit.

In distinct contrast to prior-art apparatus, the aforementioned structure defining said conduit comprises material having electrical resistivity less than or equal to that of the liquid particle-suspending medium over the entire length of the conduit it defines. Preferably, said structure comprises a single wafer of uninsulated electrically conductive material, e.g., tungsten or platinum, having a small, hydrodynamically smooth through-hole formed therein, such through-hole defining the conduit through which the liquid suspension of particles is made to pass. Alternatively, the structure comprises a plurality of contiguous wafers, each having an electrical resistivity less than or equal to that of the particle-suspending medium, and one of such wafers having a resistivity substantially less than that of the other wafers. The operative distributions of the electric field near and in the sensing conduit, and thereby the operative characteristics of the new apparatus, arise in the interaction of said conductive material with the liquid particle-suspending medium in which the particles are suspended. Through appropriate selection of operational parameters the sensing conduit may be caused to provide increased sensitivity to particle characteristics other than physical volume.

Yet another aspect of the invention is the provision of a novel method for sensing and characterizing particles in which the particles to be characterized are suspended in a liquid medium having electrical impedance per unit volume which differs from that of the particles and passed substantially one at a time through the sensing structure of the invention while changes in a pre-established electrical current through such conduit are monitored.

The invention and its advantages will be better understood from the ensuing detailed description of preferred embodiments, reference being made to the accompanying drawings in which like reference characters denote like parts.

BRIEF DESCRIPTION OF THE DRAWINGS

FIGS. 6A and 6B illustrate front and longitudinal section views of a third embodiment of the new particle-sensing structure.

FIGS. 8A and 8B illustrate longitudinal sections through the sensing conduits of additional embodiments derived from particle-sensing structures illustrated in FIGS. 3 and 5, respectively.

DETAILED DESCRIPTION OF PREFERRED EMBODIMENTS

As noted above, an important object of this invention is to provide a novel apparatus for sensing and characterizing particles, said apparatus offering increased sensitivity to particle characteristics other than physical volume.

Apparatus Embodiment 1

Figure 1:
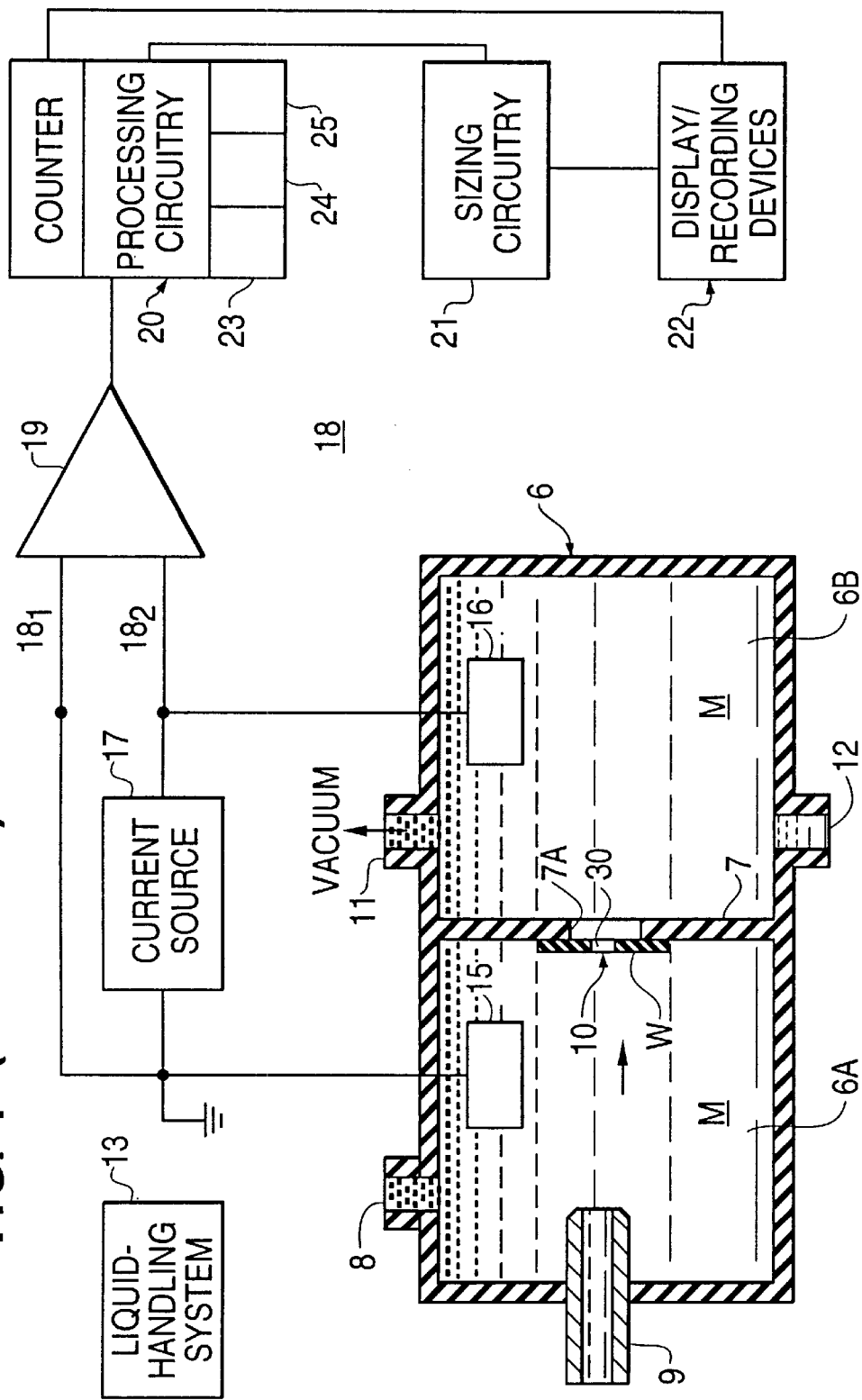
FIG. 1 illustrates a prior-art apparatus for sensing and characterizing particles by the Coulter principle.
Figure 2:
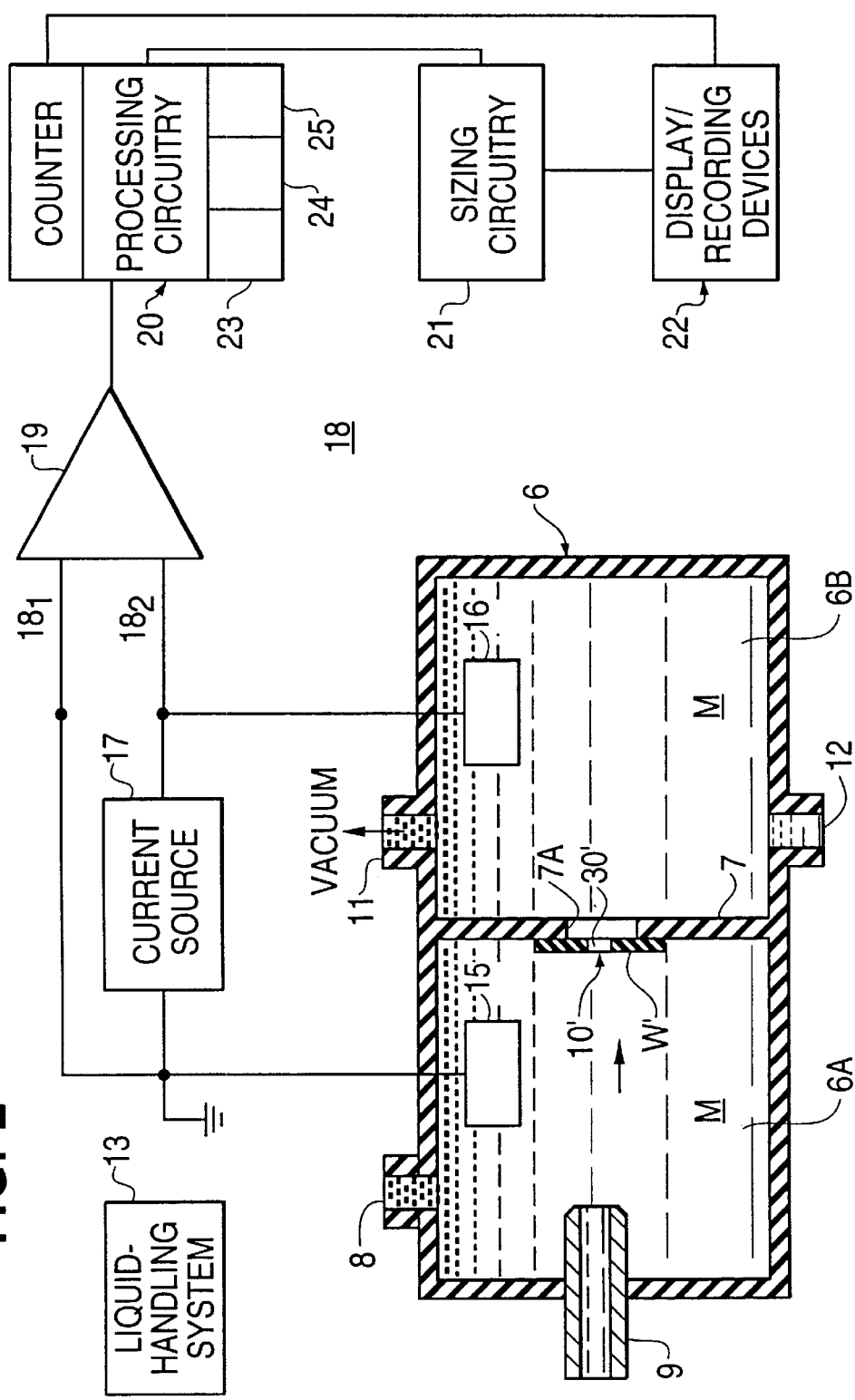
FIG. 2 illustrates a first embodiment of a new apparatus for sensing and characterizing particles; conventional means for controlling temperature of medium M is not indicated.

In FIG. 2 is schematically illustrated, in accordance with a preferred embodiment of the invention, a new apparatus for sensing and characterizing particles. As in the Coulter apparatus of FIG. 1, the apparatus of the invention comprises a dual-compartment dielectric vessel 6 which defines first and second compartments 6A and 6B separated by a dielectric wall 7. Each of said compartments 6A and 6B is adapted to contain, and is filled with, a liquid medium M having electrical impedance per unit volume that differs from that of the particles to be characterized. In general any liquid media (either aqueous or nonaqueous) comprising ionic species may be useful in specific applications of the new apparatus. Thus, many of the liquid media (e.g., isotonic saline) used with Coulter apparatus will find direct application.

A novel particle-sensing structure W', preferably provided as a small independent structure (e.g., as a wafer or disc of appropriate dimensions), is sealed over relatively large opening 7A in dielectric wall 7 and is substantially immersed in and surrounded by the liquid medium M filling both compartments of vessel 6. The hydrodynamically smooth wall 30' of a small through-hole transpiercing sensing structure W' defines a particle-sensing conduit 10' which is caused to constitute the only operative fluidic connection between compartments 6A and 6B. As discussed in detail below, the novel structure of sensing structure W' is caused to provide wall 30' of conduit 10' with a single axisymmetric, delimited region of electrical resistivity substantially less than that of suspending medium M, said conduit wall having electrical resistivity less than or equal to that of the medium M over the entire length of said conduit.

Particles to be sensed and characterized are suspended at an appropriate concentration in a suitable liquid medium, e.g., liquid medium M. The suspension medium may be selected to meet the requirements of a specific application and need not be limited to those presently in use with Coulter apparatus. The particle suspension is introduced into compartment 6A through a suitable inlet port 8 (or 9) formed therein. A vacuum, provided by an appropriate source in liquid-handling system 13 and operatively coupled to an outlet port 11 suitably formed in compartment 6B, causes the particle suspension to flow from compartment 6A into compartment 6B through conduit 10'. Each particle in the suspension displaces its own volume of liquid medium M, and if the dimensions of conduit 10' and the concentration of particles in the suspension are appropriately selected, particles can be made to transit conduit 10' more or less individually. Excitation electrodes 15 and 16 are positioned in respective compartments 6A and 6B. Electrodes 15 and 16 are operatively connected to a source 17 of electrical current, whereby a nominal electrical current is caused to flow through conduit 10' simultaneously with the particle suspension. As in the Coulter art, conduit 10' constricts the hydrodynamic field established in liquid medium M, so that wall 30' of conduit 10' surrounds and confines the flow of particle suspension between compartments 6A and 6B. In contrast to the Coulter art, the single axisymmetric, delimited region of lesser electrical resistivity comprised in wall 30' permits a portion of the excitation current to bypass conduit 10' in a functionally advantageous manner.

Current source 17 is preferably a constant-current source, so that the current it supplies is substantially independent of changes in impedance between electrodes 15 and 16 (e.g., due to substitution of conduits 10' having different diameters or lengths, temperature-induced changes in the resistivity of particle-suspending medium M, or substitution of a suspending medium M having a different resistivity). Less preferably, current source 17 may be a voltage source having high internal impedance. Current source 17 may be caused to provide a DC current, an AC current, or a combination of DC and AC currents. Sensing circuitry 18, also operatively connected to excitation electrodes 15 and 16, operates to sense and process pulsations in current between these electrodes occasioned by the passage of particles through conduit 10'. Thus, as individual particles pass through conduit 10', AC-coupled sensing circuit 19 produces an electrical signal pulse having an amplitude and/or shape characteristic of the particle's interaction with the operative electric field near and in sensing conduit 10'. It is preferred, but not required, that sensing circuit 19 have low input impedance compared to the conduit impedance. Additional circuits 20 process the particle signal pulses to provide a count of particles exceeding some particular characteristic threshold, i.e., in pulse amplitude or in pulse width at various proportions of pulse amplitude. If liquid-handling system 13 comprises a positive-displacement metering system, e.g., such as disclosed in aforesaid U.S. Pat. No. 2,869,078, such particle counts may be displayed or recorded in terms of particle concentration by appropriate devices 22. As with prior-art apparatus, pulse-editing circuitry responsive to artifactual pulses originating in recursing particles (24) or particle coincidence (25) may be desirable, or use of hydrodynamic suspension injection through flow director 9 or particle-free sweep flow via inlet 12 may be beneficial. In brief, except for sensing structure W' and functional properties of conduit 10' thereof, the apparatus of FIG. 2 may be substantially any prior-art apparatus operating according to the Coulter principle.

For example, experimental instrumentation was based on unmodified commercial particle-characterizing systems made by Coulter Corporation. Three multiple-threshold systems in which current source 17 has a high internal impedance according to aforesaid U.S. Pat. No. 3,259,842 (a Coulter Model ZB Coulter Counter coupled to a C1000 Channelyzer, a Coulter Model ZM Coulter Counter coupled to a C256 Channelyzer, and a Coulter Multisizer system) were used. All systems include electrodes 15 and 16 of metallic platinum or palladium to which current source 17 and sensing circuitry 18 are operatively connected. All systems include a liquid-handing system 13 according to aforesaid U.S. Pat. No. 2,869,078 and so do not include provisions for either hydrodynamically injected suspension flow through flow director 9 or particle-free sweep flow through port 12. However, in all systems, conduit tubes according to aforesaid U.S. Pat. No. 2,985,830 are adapted to liquid-handling system 13, and all systems do comprise a switchable edit function responsive to pulses originating in particle wall trajectories (23). All systems gave similar particle-characterization results, the major distinction being in the ease with which experimental protocols could be implemented. A system providing precise incremental control over the current supplied by current source 17 is preferred, e.g., the Coulter Model ZM Coulter Counter.

For the present work, the conventional Coulter wafer (W in FIG. 1) was removed from damaged conventional conduit tubes and replaced by a sensing structure (W' in FIG. 2), sealed to the tube with commercial epoxy adhesive. Some of the modified conduit tubes were provided with a temperature-sensing element, also attached to the outer wall of the conduit tube near sensing structure W' with commercial epoxy adhesive, by which means the ambient temperature of sensing structure W' was monitored during the experimental determinations. Unless otherwise stated, commercial isotonic saline (Isoton II, Coulter Corporation; resistivity of 61.4 ohm·cm at 22° C.) was used both as liquid medium M and to suspend the particles to be characterized.

Embodiments of the Sensing Structure

In accordance with the present invention, the apparatus of FIG. 2 is characterized by a novel particle-sensing structure W'. As in the Coulter art, the material comprised in sensing structure W' is transpierced by a small through-hole of appropriate cross-section, the hydrodynamically smooth continuous wall 30' of which defines conduit 10'. It is preferred that conduit 10' comprise a continuous wall 30' defining a right cylindrical conduit of circular cross-section, preferably of diameter D between 0.010 mm and 0.400 mm, through sensing structure W'. The axis of conduit 10' coincides with the intended direction of flow therethrough and is preferably made to coincide with that of particle-sensing structure W'. Thus, wall 30' is a bore-wall and the conduit cross-section is constant along the axis. Less preferably, other diameters may be used, and prismatic or non-constant conduit cross-sections may be advantageous in some applications of such sensing structures. It is preferred, but not necessary, that sensing structure W' comprising conduit 10' be formed as an independent structure of geometry and dimension suited to the intended application.

In distinct contrast to the Coulter art, conduit 10' of sensing structure W' is not formed through a dielectric material, but comprises material having electrical resistivity less than or equal to that of particle-suspending medium M over the entire length of the conduit. Sensing structure W' is formed of solid material the electrical resistivity of which is, in the broadest sense, so selected as to cause any longitudinal section of structure W' including the axis of conduit 10' to effectively comprise a single axisymmetric, delimited region of electrical resistivity substantially less than that of suspending medium M. Although materials having a greater resistivity may be used, it is preferred that the resistivity of said delimited region be no more than 0.10 (ten percent), and most preferably no more than 0.01 (one percent), of the resistivity of liquid medium M. Consequently, hydrodynamically smooth wall 30' of conduit 10' in FIG. 2 is made to comprise a single delimited region of length L along the axis of the conduit having axisymmetric electrical conductivity which is substantially greater than that of liquid medium M. It is preferred that L is between 0.5D and 5.0D, but other L/D ratios may be useful in some applications. As will be apparent to those skilled in appropriate arts, structures incorporating the novel axisymmetric conductivity of wall 30' may be embodied by a variety of techniques in a broad range of designs and geometry.

Less apparent is the discovery that to provide a particle-sensitive field in the vicinity of conduit 10', the particular conductive material comprising conduit 10' must interact appropriately with medium M. It is preferred that the conductive material develop an substantial interphase concentration polarization layer when used as an electrode in medium M, and it is further preferred that the material have a substantial reversible potential when so used.

Sensing structures W' suitable for use in the FIG. 2 apparatus may be realized in a variety of embodiments, all of which are comprised within the foregoing generic description. It is believed that the concepts of this invention are now sufficiently described that, with the aid of preferred embodiments to follow, those skilled in the relevant arts will be able to fabricate particle-sensing structures enabling the demonstration of particle-characterization apparatus according to the invention. Sensing structures incorporating the inventive concept may be adapted by prior-art methods to enable simultaneous passage of a suitable suspension of the particles to be characterized and an electrical excitation current through the particle-sensing conduit. Although the novel particle-sensing structure may be excited by voltage sources, use of constant-current excitation sources is preferable; the excitation sources may provide a direct current, an alternating current, or a combination thereof.

Figure 3:
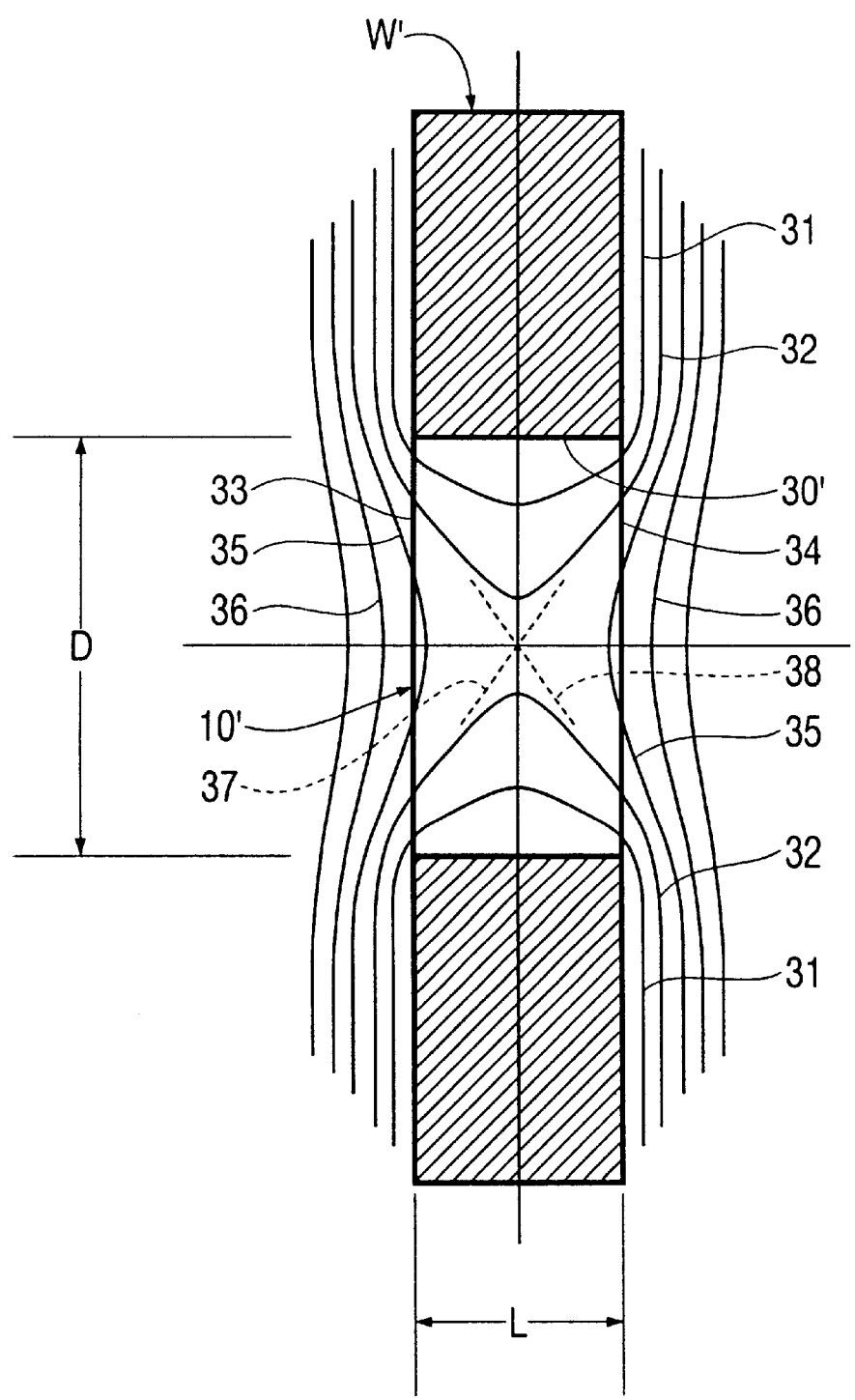
FIG. 3 illustrates a longitudinal section through the sensing conduit of a first embodiment of the new particle-sensing structure.

Embodiment 1 of the Sensing Structure:

With reference now to FIG. 3, the characterizing resistivity profile along conduit 10' is preferably realized by forming sensing structure W' from a homogeneous metal, e.g., tungsten or a metal from the platinum group. It is preferred that the material be substantially pure chemically, to avoid local differential interactions with the particular liquid medium M. It is also important that processes used to form sensing structure W' leave no residue of a second conductive material on any surface thereof expected to come into contact with medium M. Any conductive material may provide useful operational characteristics in a specific application. Examples include materials used as electrodes in the electrochemical art, e.g., glassy carbon, titanium carbide or nitride, or other metals such as gold, silver, titanium, tantalum, or their various alloys. Of interest also are the materials used in electrophysiologic electrodes, such as indium or stainless steel. A material having substantial hardness is preferred. In general, the resulting sensing structure W' may exhibit any particular detail within the range of the foregoing generic description.

The geometry of sensing structures W' is not critical to function and may be adapted as necessary. For example, sensing structure W' may take the form of a relatively thick disc of the selected material, said disc having substantially conical recesses interconnected by an conduit 10' of the desired dimensions, as is known in the Coulter art.

Sensing structure W' is preferably formed as a disc of the selected electrically conductive material, of a thickness appropriate to the intended conduit length L and of a minimal outer diameter $D_w$ approximately three times the intended diameter D of conduit 10'. Preferably, the finished thickness L of the sensing structure is in the range of 0.7 to 3.0 times the diameter D of the finished conduit 10', and the outer diameter $D_w$ is sufficient to permit convenient handling, e.g., 1.5 to 4 mm. Preferably, the disc is transpierced at an appropriate site to form a through-hole, and the through-hole is appropriately finished to generate the hydrodynamically smooth wall 30' defining conduit 10'. It is preferred that conduit 10' comprise a continuous wall 30' defining a right cylindrical conduit of circular cross-section through sensing structure W', i.e., wall 30' is a bore-wall and the conduit cross-section is constant along the axis. The disk is then finished to the desired thickness, e.g., L=D, and preferably electropolished as is known in the electrochemical art, to remove surface defects which might act as electrochemical nucleation sites. Sensing structures W' comprising some materials may benefit from specific surface treatments, e.g., passivation or electrolytic etching, as is also known in the electrochemical art.

Conduit 10' in FIG. 3 is thus defined by a continuous hydrodynamically smooth wall 30' through homogeneous conductive disk W' of thickness L, conduit 10' is thus circumferentially bounded by said uninsulated conductive material composing structure W', and the axisymmetric resistivity along wall 30' is less than that of medium M. Structures W' may be realized in a variety of embodiments that appropriately comprise conductive materials surrounding conduit 10'. As will be apparent, such structures W' only fulfill a necessary, but not a sufficient, condition for use as sensing structures W' in the apparatus of FIG. 2.

Characteristics of signal pulses generated by particles transiting conduit 10' in FIG. 2 result from a complex interaction of the particles with both the operative electric field established in the suspending medium M by the excitation current between electrodes 15 and 16 and the hydrodynamic field established by the suspending medium M carrying the particles through conduit 10'. The distribution of both the hydrodynamic through-field and the electric field in FIG. 3 conduit 10' scales with orifice diameter D and axial length L of conduit 10', and as is known in the Coulter art, both fields may be shaped by contouring orifices 33 and 34 of the conduit. While hydrodynamic characteristics of smooth continuous conduit 10' are identical to those of a traditional Coulter conduit of equivalent geometry and dimensions, the operative electric field in the vicinity of conduit 10' is more complex, both in origin and distribution, than the electric field associated with the Coulter conduit.

During operation of the FIG. 2 apparatus, sensing structure W' is immersed in liquid medium M and is coupled to the electric field established therein between electrodes 15 and 16 by current source 17. Sensing structure W' thereby assumes an independent potential and in turn superimposes equipotentials near itself in medium M. Consequently, and in contrast to the Coulter conduit 10 in FIG. 1, the resultant electric field in the vicinity of conduit 10' in FIG. 2 is substantially homogeneous for positions outside a distance 0.5D from the conduit orifices. With reference again to FIG. 3, equipotentials of the electric field are axisymmetric and of two types. Equipotentials 31 and 32 closest to sensing structure W', both in proximity and electric potential, are parallel to the sensing structure and extend through conduit 10' near wall 30', while those more remote in proximity and electric potential (e.g., 35 and 36) only inflect toward conduit orifices 33 and 34. The two equipotential forms approach each other to form a common equipotential along asymptotes 37 and 38, the latter intersecting mutually at an angle of 54.2 degrees with the conduit axis at its midpoint. In contrast to the Coulter conduit, the electric field within the geometric conduit of sensing structure W' is inhomogeneous regardless of the L/D ratio of conduit 10'. Further, the concave form of the equipotentials near conduit 10' in FIG.

3 contrasts markedly with the well-known semi-elliptical equipotentials of the Coulter conduit, which extend outward from its orifices. However, the operative electric field in the vicinity of sensing structures W' is not the electric field illustrated in FIG. 3, but that field as modified by non-scaling interphase interactions with surrounding liquid medium M carrying particles through conduit 10'.

As noted in foregoing discussion of the prior art, electrodes immersed in a liquid medium comprising ionic species interact electrochemically with the medium. Although sensing structure W' is not an electrode, due to its immersion in liquid medium M it is forced to maintain a potential intermediate between those of respective electrodes 15 and 16 in the electric field established between said electrodes by current source 17. At very low current densities between electrodes 15 and 16, the lines of current flow near sensing structure W' are perpendicular to equipotentials of the electric field, and the conductive material comprised in sensing structure W' exchanges electrons between ions in portions of medium M in compartments 6A and 6B. The primary conduction path is thus by metallic conduction through the body of sensing structure W', in parallel with an insubstantial secondary path by electrolytic conduction through conduit 10', and most of the current supplied via electrodes 15 and 16 from current source 17 thus bypasses conduit 10'. As a result, particles transiting conduit 10' do not produce signal pulses, and sensing structure W', in addition to maintaining the aforesaid equipotentials, develops at least a partial polarization layer and an overvoltage.

The spatial configuration of the polarization layer depends on the local current density, and hence the polarization layer develops preferentially around the conduit orifices where the electric-field gradients are greatest. With increasing current density in medium M, the polarization layer increases in spatial extent and thickness, and the overvoltage increases nonlinearly as the interface capacitance charges. At higher current densities, the overvoltage increasingly inhibits additional electron transfer through larger areas of the conductive material covered by the polarization layer as determined by local electric-field gradients, until conduit 10' becomes a major path of current conduction and particles transiting conduit 10' may begin producing signal pulses. In this state, the uninsulated conductive material composing sensing structure W' is at least partially insulated from medium M by the polarization layer, the spatial configuration of which is determined by the local current density. Consequently, the effective distribution of the operative electric field may be modified appreciably from that indicated in FIG. 3, and particularly for dielectric particles, at high current densities conduit 10' may behave similarly to the traditional Coulter conduit over a considerable range of current provided by current source 17. These operational characteristics of sensing structure W' are in strong contrast to those of Coulter wafer W in the apparatus of FIG. 1. In the Coulter apparatus all current consistently passes through conduit 10 regardless of the current level between electrodes 15 and 16, and there is no current-dependent polarization layer and overvoltage.

Further, the distribution of ionic species within the interface layer is determined by the polarity of the local potential gradient, and so both cations and anions comprising medium M may form gradients in the vicinity of conduit 10'. Thus, the capacitance of the interface layer may also display a position-dependent dynamic response to the passage of a particle, due to different mobilities for said cations and anions. Both the operative field distribution and the local capacitance of the interface layer, and thereby the characteristics of a signal pulse generated on passage of a particle through conduit 10', depend on the particular sensing structure W' and the electrochemical conditions in which it operates. These properties may also be influenced by the flow of medium M as it carries particles through conduit 10'.

At a given temperature the operative electric field near and in conduit 10' is therefore determined by the interaction of the conductive material comprised in sensing structure W' with the liquid medium M, and hence is dependent on properties of the particular conductive material, the dimensions of conduit 10' therethrough, the chemical makeup of the particular medium M, and the current density therein in the vicinity of sensing structure W'. For a given electrochemical system comprised of a particular medium M and a particular material surrounding conduit 10', the signal pulse generated by particles transiting conduit 10' at a given flow rate depends upon the distribution of current density in the vicinity of the conduit. The interphase effects do not scale with conduit geometry and exert their most significant effects on pulse characteristics for conduits of small diameter D. Consequently, embodiments of sensing structures W' appropriately comprising certain conductive materials will fail to respond to particles transiting conduit 10' therein, even though they are structurally similar to responsive embodiments comprising a different conductive material or conduit dimensions. The material defining said delimited conduit region is thus so selected as to provide, by interaction with the particular liquid medium M, an operative electric field near and in conduit 10' whereby the apparatus in FIG. 2 is responsive to particles transiting conduit 10'. The maximum current between electrodes 15 and 16 is limited by the reversible potential of the particular conductive material in the particular medium M; when the current density is sufficient as to cause sensing structure W' to reach this potential, electrolysis occurs and the resultant excess noise limits particle sensing. This characteristic limits electrode current to levels substantially less than that for Coulter conduits, and so the maximum amplitude of signal pulses generated by sensing structure W' is about an order of magnitude less than for Coulter apparatus.

The material-dependent trailing pulse edges seen with the new particle-sensing structure W' suggests that the particle interacts with the electrochemical conditions within conduit 10' in a rate-limited process. One possibility is that the toroidal recirculating flow pattern at the exit orifice of conduit 10' directly affects the spatial configuration of the ionic layer. A second possibility is that passage of a particle acts to discharge the capacitance of the interface layer in the vicinity of the conduit via the low-input impedance amplifier 19, with recharging of said layer being rate-limited by the mobility of the ions at the orifice of the conduit from which the particle exits. With reference to Eq. 3, particles of the same geometry and dimension, but formed of materials having substantially different conductivities, may thus provide signal pulses differing in amplitude, shape, or both amplitude and shape, depending on the specific conductive material in sensing structure W', the particular liquid medium M, and the current supplied by source 17. If the ionic species have significantly different mobilities, pulse dynamics may depend on whether particles transit the conduit with (or against) the direction of negative charge transfer. Thus, the operative field surrounding sensing structure W' in FIG. 2 is fundamentally different from the one surrounding Coulter wafer W in FIG. 1.

The ten structures W' listed in Table 1 have been evaluated for use in the FIG. 2 apparatus. These structures were made as field-amending elements in connection with cross-referenced U.S. patent application Ser. No. 08/887,588 and, being available, were tested for function as independent particle-sensing structures. The first nine entries in Table 1 are in accordance with the present embodiment, i.e., they comprise only a disc of an uninsulated, electrically conductive, homogeneous, solid material. Table 1 is not intended to be limiting with regard to useful materials, dimensions, or media M.

Each structure W' was attached to a conventional aperture tube with two-part commercial epoxy adhesive according to the manufacturer's instructions. The modified aperture tubes were substituted for the conventional aperture tube, according to aforesaid U.S. Pat. No. 2,985,830, on apparatus according to aforesaid U.S. Pat. No. 3,259,842, i.e., a Model ZM Coulter Counter system equipped with standard platinum electrodes. Conventional flow rates were established by the standard liquid-handling system, one according to aforesaid U.S. Pat. No. 2,869,078. For each structure W' the voltage-current relationship between electrodes 15 and 16 was determined by monitoring the electrode voltage with a high-impedance voltmeter while incrementing the constant current provided by supply 17. Except for substitution of structure W' for the traditional dielectric Coulter wafer, all apparatus was conventional. In some instances the temperature was monitored, either by a thermometer placed in the sample beaker or a thermal sensor fixed to the conduit tube. Observed temperatures were between 22° C. and 25° C.

Table 1.

Materials, conduit diameters D and lengths L, outer diameter $D_w$ of disc, and characteristics of experimental sensing structures W' tested in the apparatus of FIG. 2. Isotonic saline was used as medium M in the functional tests. In the "Pulses" column, d is the diameter of the latex test particle, in $10^{-3}$ mm. The "Current" column indicates the range of electrode current over which particles were detected, while the "Gassing" column indicates the approximate electrode current at which electrolysis in the conduit becomes apparent through excess noise. By way of comparison, Coulter conduits of similar dimensions (D=0.050 mm, L=0.060 mm) may be used with electrode currents of 1,500 microamps or more before Joule boiling in the conduit becomes significant.

In a second exemplary embodiment (B in Table 1), structure W' consists of a disc of tungsten 3.0 mm in outer diameter in which a cylindrical through-hole 0.100 mm in diameter was formed as is known in the art of making Coulter wafers. The tungsten disc was polished on both sides, to a finished thickness of 0.061 mm. The current-voltage relationship measured at excitation electrodes 15 and 16 is indicated by the data curve labeled "Tungsten" in FIG. 4. No electrolysis was apparent for electrode currents to 1000 microamps.

Figure 4:
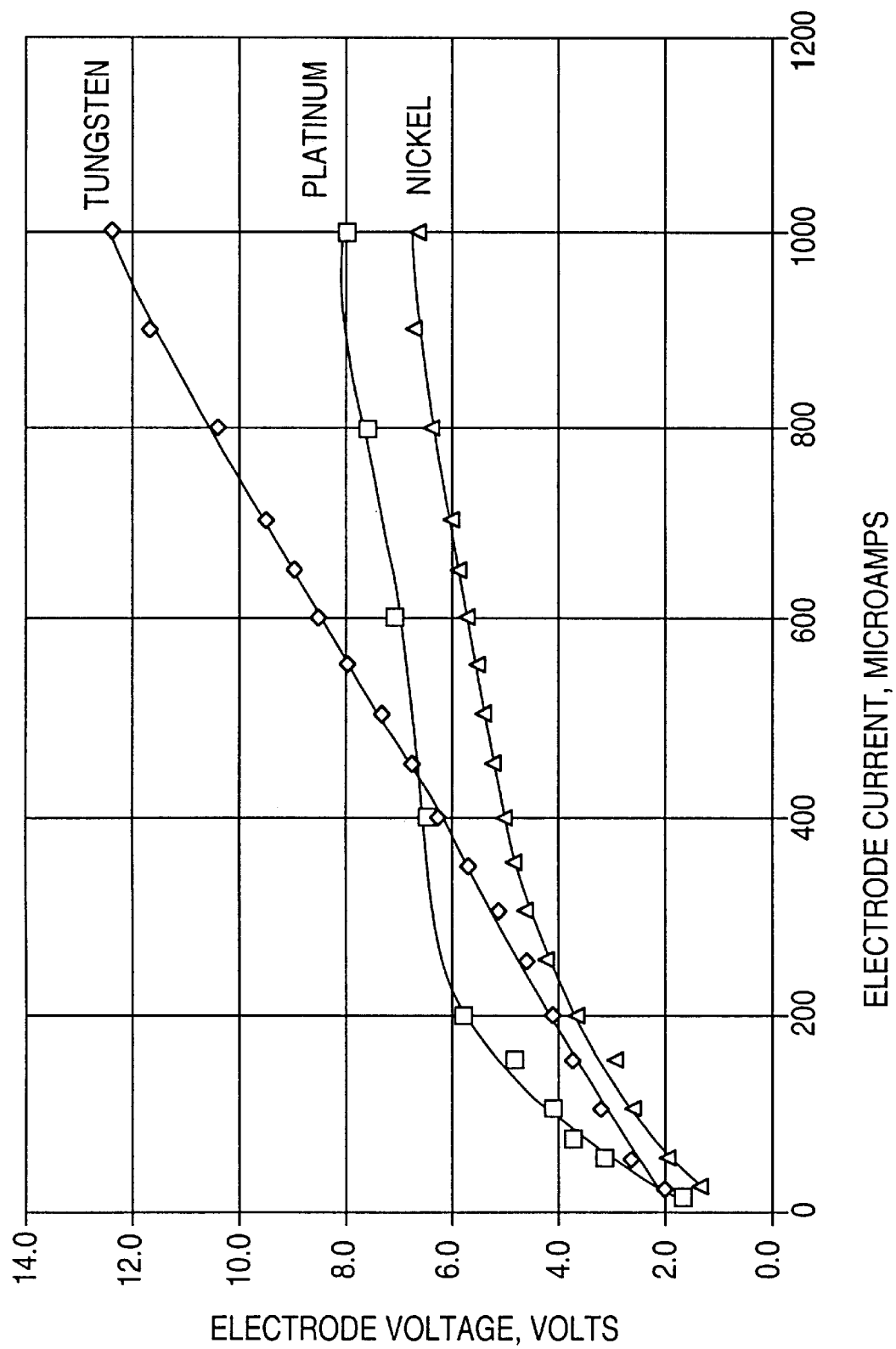
FIG. 4 illustrates the relationship between the electrode current I and voltage V for three sensing structures according to FIG. 3 when used in the apparatus of FIG. 2.

The current-voltage (I-V) characteristics measured at excitation electrodes 15 and 16 for the other structures W' listed in Table 1 were similar, and were bracketed by those for structures W' made of platinum and nickel (respective data curves "Platinum" and "Nickel" in FIG. 4). Data in FIG. 4 illustrate the range of behavior demonstrated by the structures W' listed in Table 1. The data in FIG. 4 are not corrected for polarization effects at the electrodes, i.e., there is a current-dependent contribution or offset to the measured electrode voltage due to the overvoltages of electrodes 15 and 16 in medium M.

Latex particles, approximately 0.010 mm in diameter and suspended in isotonic saline, were used to determine whether the structures W' would generate volume-related signal pulses on passage of particles through their conduits 10'. Flow rates ranged between 0.7 m/sec and 8 m/sec. Both the aforesaid exemplary embodiments (A and B in Table 1) produced clean bell-shaped pulses differing from those provided by similar Coulter conduits in these significant ways:

1. The pulse amplitudes are smaller, typically less than 70% of the amplitude the same particles generated in Coulter conduits at comparable excitation currents. The minimum detectable particle is larger than for the Coulter conduit, which for comparable conduits will detect a particle having a diameter of approximately 2% of its own diameter D. For said exemplary embodiments, particles become detectable for particle diameters between 0.006 mm and 0.007 mm, i.e., at about 12% (A in Table 1) and 7% (B in Table 1) of the respective conduit diameter. The comparative insensitivity of the platinum embodiment is

| Structure, W' | Material | D, mm | L, mm | $D_w$, mm | Pulses; d, $\mu$ | Current, $\mu$amps | Gassing, $\mu$amps |
|---|---|---|---|---|---|---|---|
| A | Platinum | 0.056 | 0.100 | 2.5 | Yes; 9.9 | 10–200 | 200 |
| B | Tungsten | 0.100 | 0.061 | 3.0 | Yes; 9.9 | 250–1000 | |
| TiC | Titanium Carbide | 0.050 | 0.063 | 3.0 | Yes; 9.9 | 20–100 | 100 |
| WC1 | Tungsten Carbide | 0.050 | 0.064 | 3.0 | No; 9.9 | | 200 |
| WC2 | Tungsten Carbide | 0.100 | 0.079 | 3.0 | No; 9.9 | | 400 |
| WC3 | Tungsten Carbide | 0.200 | 0.200 | 3.0 | Yes; 48 | 20–200 | 400 |
| WC4 | Tungsten Carbide | 0.200 | 0.241 | 3.0 | Yes; 48 | 20–200 | 400 |
| WC5 | Tungsten Carbide | 0.300 | 0.297 | 3.0 | No; 48 | | 400 |
| Ni | Nickel | 0.100 | 0.100 | 3.0 | No; 14.8 | | 50 |
| J | Platinum on ruby | 0.050 | 0.066 | 3.6 | Yes; 9.9 | 20–200 | 200 |

In a first exemplary embodiment (A in Table 1), sensing structure W' consists of a disc of platinum 2.5 mm in outer diameter and 0.100 mm thick in which a cylindrical through-hole 0.056 mm in diameter was formed as is known in the art of making Coulter wafers. The relationship between the current supplied by current source 17 and the voltage between excitation electrodes 15 and 16 is indicated by the data curve labeled "Platinum" in FIG. 4. As indicated in Table 1, at electrode currents of 200 microamps electrolysis became apparent at the conduit.

partially due to the small maximum current that can be used (about 200 microamps) before excess noise due to electrolysis becomes detrimental. However, with increased pulse amplification, pulse-height distributions can be obtained from both exemplary embodiments by conventional methods with the Model C256 Channelyzer.

2. No M-shaped pulses were observed for either of the two exemplary embodiments, and when pulse data from the Model ZM Coulter Counter are coupled to a Model C256 Channelyzer, histograms of unedited pulse heights do not show substantial highside skewness. This is in contrast to Coulter conduits, in which M-shaped pulses arise when particles transit the conduit on trajectories through the high gradients in the electric field near the conduit wall. Thus, as suggested by equipotentials 31 and 32 in FIG. 3, the operative field near and through conduit 10' contains substantially smaller field gradients at the conduit orifices than exist for the Coulter conduit. Pulses from recursing particles, if present, are lost in noise.

3. The rise times of the leading edges of signal pulses from both exemplary sensing structures W' are similar, both to each other and to those given by Coulter conduits, but the fall times of the trailing pulse edges from both are substantially slower than those given by the Coulter conduit. Further, the fall times of trailing edges of pulses given by sensing structure W' made of tungsten (B in Table 1) are substantially slower than those given by sensing structure W' made of platinum (A in Table 1). These differences are sufficient to permit demonstration on a histogram of pulse-widths taken at a given portion of pulse heights.

With the exception of the last entry in Table 1, the other structures W' do not function as well as the two exemplary embodiments. Sensing structure W' made of titanium carbide (TiC in Table 1) gives pulses similar to those from the two exemplary embodiments, but of smaller amplitude, and the low limit placed on excitation current by onset of electrolysis makes the pulses difficult to extract from conduit noise. A sequence of structures W' made from tungsten carbide (WC1 through WC5 in Table 1) was tested, to see if the poor particle response could be improved through geometric scaling; although small pulses were generated, the diameter of the minimum detectable particle was only about 25% of the conduit diameter D. No pulses could be detected for the structure W' made of nickel (Ni in Table 1), due to the low current level at which electrolysis began.

All of the structures W' except B listed in Table 1 were also tested in 4% saline, with some improvement in the performance of those made from platinum (A) and titanium (TiC). For these latter, the respective excitation currents could be increased to 500 microamps and 200 microamps before excess noise due to electrolysis became detrimental. In this more conductive medium M, particles having approximate diameters of 0.004 mm and 0.010 mm were detectable by the respective sensing structures.

Embodiment 2 of the Sensing Structure:

Sensing structure W' may be formed from one material and provided with a conductive coating or plating of a second material, thereby providing combinations of material properties unobtainable with the individual materials. For example, due to the relative softness of the metallic alloy, the aforesaid platinum sensing structure W' may be damaged in clearing a clogged conduit. A sensing structure W' combining improved resistance to deformation with the electrical properties of a platinum alloy is desirable, and other applications of the FIG. 2 apparatus may benefit from sensing structures W' providing other combinations of material properties. In general, the conductive material may be selected as for Embodiment 1 of the Sensing Structure, and the resulting sensing structure W' may exhibit any particular detail within the range of the foregoing generic description.

Figure 5:
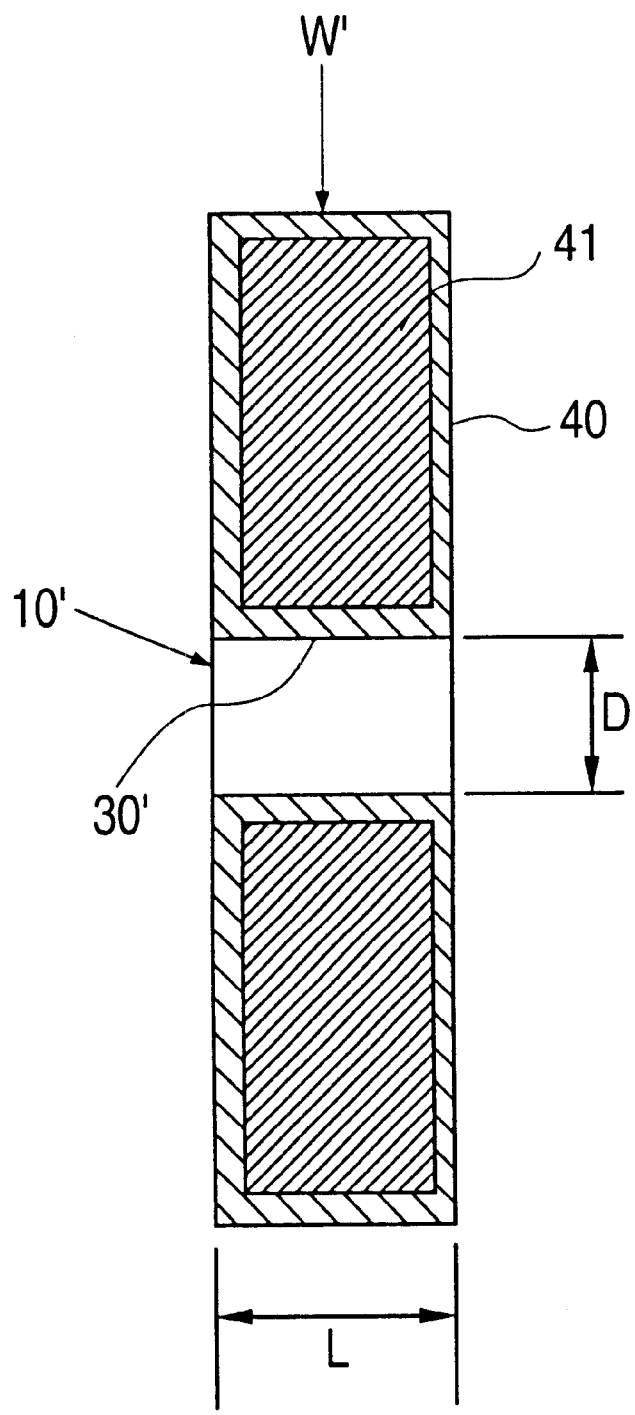
FIG. 5 illustrates a longitudinal section through the sensing conduit of a second embodiment of the new particle-sensing structure.

With reference to FIG. 5, sensing structure W' according to the present embodiment comprises a cladding, coating, or plating layer 40 of an appropriate conductive material on a substrate 41 of a second material providing a desired physical property and shaped to provide the desired geometry. The geometry of sensing structures W' is not critical to function and may be chosen as convenient to the application. Conduit 10' of sensing structure W' is preferably formed as a hydrodynamically smooth circular through-hole in a disc of the selected substrate material, at least the wall of said through-hole then being cladded, coated or plated with a layer 40 of sufficient conductivity as to provide a conduit wall 30' having resistivity less than that of the medium M it surrounds. It is preferred that substrate 41 be made of a dielectric material and that the material used to form conductive layer 40 be chemically pure, whereby electrochemical nucleation sites due to pin-holes and impurities in conductive layer 40 are avoided. Conductive layer 40 may be formed by any appropriate method known in the cladding, coating or plating art and is preferably continuous and defect free. It is preferred that the conductive layer 40 extend outward on the face of substrate 41 sufficiently far from the through-hole as to substantially provide the electric field distribution illustrated in FIG. 3, i.e., for a minimal distance equal to about three conduit diameters D outward from the edge of the through-hole. Conductive layer 40 need not be uniformly thick over the surfaces of substrate 41, and for some applications it may be advantageous to selectively control the thickness of said layer to provide a variation in the apparent resistivity thereof. Some of the benefits of the invention may be obtained if conductive layer 40 is restricted to the surface of said through-hole.

Conduit 10' in FIG. 5 is thus defined by a continuous hydrodynamically smooth wall 30' cladded, plated or coated by homogeneous metallic material 40, conduit 10' is thus circumferentially bounded by said uninsulated conductive material 40, and the axisymmetric resistivity along wall 30' is less than that of medium M. It is preferred that uninsulated conductive material 40 extend continuously outward from conduit 10' onto the contiguous surfaces of the substrate comprising conduit 10' to include the surrounding surface area to a minimal radial distance of three conduit diameters.

An illustrative sensing structure W' (J in Table 1) according to the present embodiment was formed from a traditional Coulter wafer 41 having a conduit 0.100 mm in diameter, the wafer being made as a ruby disc 3.6 mm in outer diameter and polished to 0.050 mm in thickness. The central conduit was filled with commercial platinum paint used to apply electrodes to glass, and the paint was cured according to the manufacturer's instructions. The entire ruby disc was then coated with the platinum paint and the paint cured. A new central conduit was then formed in the platinum core filling the original conduit and finished to a diameter of 0.050 mm as is known in the Coulter art. Consequently, a cladding layer 40 of conductive platinum approximately 0.025 mm thick was left on the wall of the original conduit. Both faces of the clad ruby disc were then polished to smoothness, to a final thickness of 0.066 mm, so that each face was cladded by a platinum layer 40 approximately 0.008 mm thick. The finished sensing structure was then fixed to a conventional conduit tube with commercial two-part epoxy adhesive used according to the manufacturer's instructions.

When tested in the FIG. 2 apparatus, this embodiment of sensing structure W' gave results that were substantially identical to those for the preceding embodiment made from solid platinum (A in Table 1), except that slightly higher currents were required before detectable signal pulses were obtained for latex particles 0.0099 mm in diameter. Although ruby was here used as the dielectric substrate, other dielectric materials such as sapphire, silicon dioxide, or glass may also be used, as may various ceramics. Less preferably, the substrate may be made from a conductive material such as titanium carbide. Similarly, cladding materials other than platinum may be desirable or advantageous in some applications of the new apparatus.

The I-V characteristics of structures W' are in general logarithmic, but over the ranges of current variation produced by particles transiting the conduits thereof, the incremental resistance is functionally linear. Consequently, novel sensing structures W' according to FIG. 3, made in a variety of dimensions and electrically conductive materials, and FIG. 5 permit sizing of dielectric particles when used in the apparatus of FIG. 2.

However, functional behavior of sensing structures W' is quite different from that of Coulter conduits in significant ways. As indicated in Table 1, in isotonic saline the platinum sensing structures W' (A and J in Table 1) generate pulses over a useful current range between approximately 20 and 200 microamps; in comparison, the tungsten embodiment (B in Table 1) generates useful pulses over a current range from approximately 250 microamps upward. As illustrated by the respective data curves in FIG. 4, the platinum embodiments operate in the nonlinear portion below the knee of the I-V characteristic, whereas the tungsten embodiment operates in the linear portion above said knee. The incremental resistance for sensing structures W' may be estimated as the slope of the respective data curve in FIG. 4, and for the platinum embodiments is in the range of 16,000 ohms to 20,000 ohms in the useful region of the characteristic curve. A similar calculation for the tungsten embodiment gives a linear resistance of about 11,200 ohms over the current range for which pulse data were taken.

The electrical resistance of the liquid column within a geometric conduit 10' is given by Eq. 1, and for isotonic saline as medium M, is approximately 24,930 ohms, 4,770 ohms, and 20,640 ohms for conduits in sensing structures W' : A, B, and J, respectively, in Table 1. As has been noted, the measured resistance of Coulter conduits is substantially greater than this geometric value, and is closely correlated to actual measurements via Eq. 2. For Coulter conduits having the dimensions of the conduits in sensing structures W' : A, B, and J in Table 1, conduit resistances of 32,430 ohms, 8,970 ohms, and 29,040 ohms, respectively, would be expected. The apparent resistance (16,000 to 20,000 ohms) of the conduit in the platinum embodiments is less than the resistance of the liquid column in the conduits (25,000 ohms and 20,640 ohms, respectively, for A and J), whereas that of the tungsten embodiment (11,200 ohms) is greater than that for a Coulter conduit of the same dimensions (8,970 ohms). If the approach underlying Eq. 2 is applied to the measured resistance of the latter embodiment, the uniform cylindrical resistance requires 0.8226D additional length to account for the measured resistance, compared to 0.5374D for the Coulter conduit. A possible explanation for these observations is that at least a portion of the current between electrodes 15 and 16 is metallically conducted through the body of the platinum embodiments rather than passing by electrolytic conduction through the conduits. In contrast, the fact that the apparent resistance of the conduit in the tungsten embodiment exceeds that of the comparable Coulter conduit suggests not only that metallic conduction occurs does not occur, but that electrolytic conduction through the conduit is inhibited. Consequently, the operative electric fields may be substantially dissimilar for the two exemplary embodiments (A and B in Table 1), that for the platinum embodiment somewhat resembling the one in FIG. 3 and that for the tungsten embodiment possibly more resembling one for the Coulter conduit.

Whereas for the Coulter apparatus the conduit contribution to impedance between electrodes 15 and 16 arises in the resistance of the restricted ohmic conductivity through the conduit, in the new apparatus the contribution from conduit 10' comprises the parallel combination of the charge-exchange resistance and capacitance of the polarization layer at the surface of sensing structure W'. The observed response to the passage of a particle thus depends not only the ohmic conductivity through conduit 10', but on contributions from the charge-exchange resistance, the capacitance of the polarization layer, and the overvoltage, all of which depend on material, electrolyte, and field distribution. In addition, the diffusion required to move ions away from said surfaces is dependent on the ionic mobility of the cations and anions in flowing medium M and so add effective serial impedances due to the ionic movement. These effects occur at each surface of sensing structure W' and so may differ in compartments 6A and 6B, with consequent differences in the respective contribution to total impedance measured at electrodes 15 and 16. There is no reason that such effects be symmetric about the midpoint of conduit 10', either in spatial configuration or ionic distribution, and both these parameters are expected to depend upon the direction and magnitude of both current and suspension flow through the conduit. The observed material-dependent differences in pulse rise and fall times is consistent with sensing structure W' providing reactive components in the impedance of conduit 10' that are not present in the impedance seen for Coulter conduits.

In the experimental apparatus, electrodes 15 and 16 were formed of untreated platinum. However, any of the materials used as electrodes in the electrochemical art could be useful in a specific application of the FIG. 2 apparatus, and it is preferred that electrode materials be chosen so that the contribution of reactance between electrodes 15 and ≠from electrode interphase processes in medium M be minimized. Thus, use of relatively nonpolarizable materials, or surface treatments resulting in increased effective electrode surface area such as platinization or electrolytic etching, would be preferable to use of untreated platinum, if stable interphase chemistry were also provided. For example, electrodes 15 and 16 made of electrolytically etched aluminum can provide more repeatable pulse-width determinations when isotonic saline is used as medium M, whereas etched ones made of indium may reduce total electrode contributions to impedance measured between the electrodes. Some applications of the new apparatus may benefit from a judicious mismatch in electrode materials or surface treatments.

The foregoing comments regarding impedance manifestations of the material of sensing structure W', as measured between electrodes 15 and 16, apply in principle as well to the material of particles transiting conduit 10'. However, such particle effects are several orders of magnitude below those seen for sensing structure W', and while the apparatus of FIG. 2 permits demonstration of a new method of particle characterization, it also demonstrates need for improved temperature control in the vicinity of sensing structure W'. For example, data in FIG. 4 were taken with variations in ambient temperatures of about 3° C. and show deviations from the expected logarithmic relationship between electrode current and voltage. It is known that the resistivity of isotonic saline has a temperature coefficient of about 2%/° C. of temperature change, and it is probable that other aspects of the interphase chemistry demonstrate similar temperature sensitivity. It was found that by surrounding the vessel from which the particle suspension was drawn with a bath containing crushed ice in water, the I-V characteristics of sensing structures W' in 4% saline became a close fit to the expected logarithmic relationship, and the dispersion in particle pulse data could be substantially reduced. For optimal performance of the apparatus in FIG. 2, it is preferred that the temperature of liquid medium M surrounding sensing structure W' be regulated, and some applications may benefit from individual control over the temperature on each face of said sensing structure, e.g., of compartments 6A and 6B and the portions of medium M contained therein. (For illustrative clarity, conventional means for such temperature control is not indicated in FIG. 2.)

In the experimental apparatus, current source 17 provided a direct current of reversing polarity, and sensing circuitry 18 was responsive to the product of excitation current and the change in impedance between electrodes 15 and 16 occasioned by a particle transiting conduit 10'. Thus, estimation of the reactive contributions to the resulting pulse must depend on time-domain measurements of pulse dynamic characteristics, e.g., rise and fall times. It is preferable that current source 17 be caused to provide an excitation current comprising at least one alternating-current component of an appropriate frequency and that sensing circuitry 18 be responsive to the temporal relationship between the voltage and current measured at electrodes 15 and 16, i.e., to the phase relation therebetween. For such applications, an appropriate frequency is preferably one no more than a few hundred Hertz, so that the effects of polarization are not negated. It may be desirable to cause current source 17 to sweep the frequency of said alternating current component from a few Hz to, say, 2 KHz, either as an aid to characterizing the interaction between a particular sensing structure W' and medium M or as a method of further characterizing a particle suspension. In some applications of such apparatus it may be desirable to use an alternating-current component having a non-sinusoidal waveform.

Facilitating art developed in reaction to the limitations of Coulter conduits may be useful in some applications of the new particle-characterization apparatus. In particular, pulse-editing circuitry responsive to artifactual pulses originating in particle coincidence (25 in FIG. 2) may be of substantial value. The low pulse signal-to-noise ratios obtained with apparatus of APPARATUS EMBODIMENT 1 do not permit recursing particles to produce significant extraneous-pulse interference, and neither pulse-editing circuitry 24 responsive to artifactual pulses originating in recursing particles nor particle-free sweep flow via inlet 12 offers real benefit. Because no anomalous M-shaped pulses were observed in experimental work, it is less apparent that use of hydrodynamic suspension injection through flow director 9 in FIG. 2 may be advantageous.

However, as has been noted functional properties of the polarization layer surrounding at least part of sensing structures W' depend on the dynamic interaction of the conductive material therein with medium M, and further, on the dynamics of ionic movement in the vicinity of such sensing structures. Consequently, flow of particle suspension through conduit 10' in FIG. 2 may exert a significant influence on ionic distribution and concentration, via convective and thermal effects on ionic diffusion in the interphase layer, with consequent loss of consistency in pulse characteristics. Thus, in some applications it may be beneficial to provide controlled operative conditions near and in conduit 10', by introducing through inlet port 8 a sheath-flow of liquid medium M at a selected temperature and hydrodynamically injecting the particle suspension as a core-flow via director 9. Other applications may benefit from injecting the particle suspension through inlet port 8 so that the particles are entrained in the sheath flow closest to wall 30' of conduit 10' and providing particle-free liquid core flow through flow director 9. While it is preferred that the particles to be characterized be suspended in medium M, it is only required that the suspending and particle-free media be compatible, not identical, in chemical makeup. It may be advantageous in the latter embodiment, therefore, to provide a particle-free liquid having electrical resistivity comparable to that of the particles, whereby sensitivity to particle characteristics may be enhanced. In yet other applications it may be beneficial to provide particle suspension at a different temperature. Consequently, it may be that in the FIG. 2 apparatus the particles, the particle-sensing structure W', electrode 15, and electrode 16 each be provided a different electrochemical or thermal environment.

Embodiment 3 of the Sensing Structure:

Sensing structures W' according to the preceding embodiments comprise the characterizing axisymmetric delimited region of low resistivity along conduit 10' as a result of the physical geometry of an individual material, but a composite structure may also provide the characterizing resistivity region. In cross-referenced U.S. patent application Ser. No. 08/887,588 there is described a method for amending the fields in the vicinity of a Coulter volumeter conduit, one aspect of said method reducing the number of particles transiting the conduit on trajectories through its high-gradient regions. The field-amending method depends on providing regions of differing electrical resistivity along the length of the particle-sensing conduit so as to make the sensitive zone of the conduit independent of its conduit fluidic length and so permit placement of the sensitive zone at a desired location within the fluidic length. For some applications of the apparatus in FIG. 2, a novel field-amending structure may permit acceptable performance without requiring hydrodynamically-focused suspension flow through flow director 9.

With reference now to FIGS. 6A and 6B, the electrical resistivity of the solid material of which sensing structure 50 is formed is, in the broadest sense, made to vary in a substantially axisymmetric manner along the axis of conduit C. Specifically, the electrical resistivity of the solid material surrounding conduit C is preferably so selected as to cause any longitudinal section of sensing structure 50 including the axis of conduit C to effectively comprise an axisymmetric, delimited central region (W' ) of high electrical conductivity which is smoothly contiguous on both its axially opposing boundaries to distal regions (52 and 53) of greater electrical resistivity. Such axial gradients in axisymmetric resistivity may be formed through mechanical assembly and joining of individual discrete elements having appropriate unequal (but substantially uniform) individual resistivities, into a composite unitary structure. For example, the conductive region may comprise a material selected as described in Embodiment 1 of the Sensing Structure and may exhibit any particular detail within the range of the foregoing generic description. The distal regions are preferably made to have an electrical resistivity substantially equal to that of the particular liquid medium M it is desired to use in characterizing the particles, e.g., for Isoton II, 61.4 ohm·cm. Thus, the unitary sensing structures comprise material having electrical resistivity less than or equal to that of the particle-suspending medium over the entire length of the particle-sensing conduit. In some applications it may be desirable that said structures have, in whole or in part, a relative dielectric constant substantially equal to that of the medium, i.e., for the same example, 78.

In principle, sensing structure 50 comprises sensing structure W' and contiguous distal elements 52 and 53, through-holes in which smoothly align with orifices 33 and 34 of conduit 10' in structure W' to form conduit C. However, it is most important that the conduit C be fluidically continuous and hydrodynamically smooth throughout its length, and it is preferred that the individual elements be made unitary into a composite structure prior to generation and finishing of conduit C. Thus, a disc of the conductive material selected to become sensing structure W' is prepared and finished to the desired thickness L. Distal elements 52 and 53 are preferably prepared as discs having the desired resistivity, a diameter at least several times the diameter of the intended particle-sensing conduit, and a thickness appropriate to the desired respective finished thickness $L_1$ or $L_2$. Said distal elements are appropriately fixed to sensing structure W' to form a unitary structure 50, e.g., via use of a conductive epoxy suitably filled with a powder of the material composing future sensing structure W'. Structure 50 is transpierced by a small through-hole, which is then finished to the desired conduit diameter as is known in the Coulter art. The axis of conduit C coincides with the intended direction of flow therethrough and is preferably made to coincide with that of sensing structure 50. The outer faces of distal elements 52 and 53 are then finished as is known in the Coulter art, to provide the desired lengths $L_1$ or $L_2$ along the wall of conduit C.

Conduit C in FIGS. 6A and 6B is thus defined by the continuous hydrodynamically smooth wall through structure 50, said wall comprising wall segment 58 through distal element 52, conduit 10' through sensing structure W', and wall segment 59 through distal element 53. Consequently, conduit 10' is circumferentially bounded by uninsulated conductive material having resistivity less than or equal to medium M, and the smoothly continuous wall of conduit C is made to have axisymmetric electrical resistivity which is caused to effectively vary in the desired manner along the axis of the conduit. By thus causing the electrical resistivity of distal regions 52 and 53 to be substantially the same as that of medium M, the distribution of the electric field in and near conduit C is substantially unaffected by the presence of the distal regions and the sensitive zone of the conduit may be located as desired within the fluidic length ($L_1+L+L_2$). In effect, distal regions 52 and 53 are made to be indistinguishable from liquid medium M insofar as the electric field surrounding sensing structure W' is concerned, that is, the electric field distribution surrounding the conductive material is substantially as illustrated in FIG. 3, and the electrical length of conduit C is thereby decoupled from its fluidic length.

In addition, except through conduit portion 10' regions of the electric field having gradients is not accessible to ions in medium M, limiting the spatial extent of the interphase polarization layer and thereby its capacitance. In this regard, sensing structure 50 functionally resembles sensing structure W' described in Embodiment 2 of the Sensing Structure, in which the conductive plating or coating is applied only to wall 30' of conduit 10'. However, sensing structure 50 is producible by methods yielding better control of critical parameters.

Sensing structure 50 may be directly substituted for sensing structure W' in FIG. 2. Some advantages of the various forms of novel sensing structure 50 may be obtained if either structure 52 or 53 is omitted. As will be appreciated, such omission will affect both the hydrodynamic field and polarization layer at the respective orifice of conduit portion 10' from which the element is omitted.

Sensing structures according to the present embodiment differ significantly from volumeter assemblies of the cross-referenced U.S. patent application Ser. No. 08/887,588, now issued as U.S. Pat. No. 6,111,398. In the latter, the central region (analogous to W') is highly resistive rather than conductive, and the distal regions (analogous to 52 and 53) are highly conductive rather than substantially equal to medium M in resistivity. Consequently, volumeter assemblies of the related application amend both the electric and fluidic fields in and near the particle-sensing conduit; the electric field, while significantly reduced in comparison with that of the traditional Coulter conduit, remains convex outward from the orifices of the functional Coulter conduit, and the fluidic field is permitted to become quasi-laminar. With regard to sensing structure 50 it is preferred to amend only the fluidic field through conduit C, so that the desired degree of laminarity through conduit portion 10' is achieved through selection of an appropriate thickness L, for element 52. The method whereby this may be done is discussed in detail in cross-referenced U.S. patent application Ser. No. 08/887,588, as is the method for reducing the effects of particles on recursing trajectories via similar selection of the thickness $L_2$ of element 53. As will be apparent to those skilled in the appropriate arts, sensing structures incorporating the characteristic axial variation in axisymmetric resistivity of wall 30' may be embodied in a range of designs, geometries, and materials.

Such sensing structures also differ significantly from the volumeter assemblies described in aforesaid U.S. Pat. No. 4,161,690. Firstly, according to said patent the particle-sensitive conduit penetrates a three-layer structure comprising a conductive layer in contact with an insulative layer on each major surface; the electrical and fluidic length L of the conduit is the combined thicknesses of the three layers. In contrast, due the resistivity of the distal elements approximating closely that of medium M, composite sensing structure 50 has an electrical thickness that equals length L of conduit portion 10' through the conductive element, while the fluidic length equals the combined thicknesses ($L+L_1+L_2$) of the respective conductive and two distal elements. Secondly, in the prior-art assembly the thickness of the conductive layer is said to be small in relation to length L of the conduit, the composite structure being designed so that the resulting conduit approximates a Coulter conduit. In contrast, the electrical thickness of sensing structure 50 consists functionally of the conductive element W', the thickness of which is at least one-half of the diameter D of conduit 10'. Thirdly, the insulative layers are said to be fiberglass reinforced plastic, which has a resistivity many orders of magnitude greater than the resistivity of media M used in Coulter apparatus, whereas in sensing structure 50 the analogous elements are made to have electrical resistivity substantially equal to that of such media. Finally, whereas the conductive layer in composite volumeter assemblies according to U.S. Pat. No. 4,161,690 functions as an electrode used so as to minimize electrochemical effects, the analogous component in sensing structure 50 independently functions to establish an advantageous polarization layer, whereby a non-volumetric sensing capability is enabled.

In summary, the preceding embodiments illustrate the characterizing difference between the new particle-sensing structure and Coulter volumeter structures of the prior art. In each embodiment the electrical resistivity of all material forming the functional structure is less than or equal to the resistivity of the medium in which are suspended the particles to be sensed and characterized. In each embodiment the characterizing axisymmetric, delimited region has electrical resistivity that is substantially less than the resistivity of said medium. And in each embodiment, the characterizing region of high electrical conductivity functions independently to provide advantageous characteristics responsive to particles transiting conduit 10'. Sensing structures according to these embodiments may be advantageously modified to perform other functions, as will be discussed in connection with the following apparatus embodiment.

Apparatus Embodiment 2

In the apparatus of FIG. 2, signal circuitry 18 is connected between excitation electrodes 15 and 16 as in the '508 patent, and the small impedance changes responsible for signal pulses are superimposed on the large and complex impedance existing between said electrodes. It is preferable that sensing circuitry respond differentially to particle-induced impedance changes, whereby may be provided an improved signal-to-noise ratio for the particle signal pulses.

Figure 7:
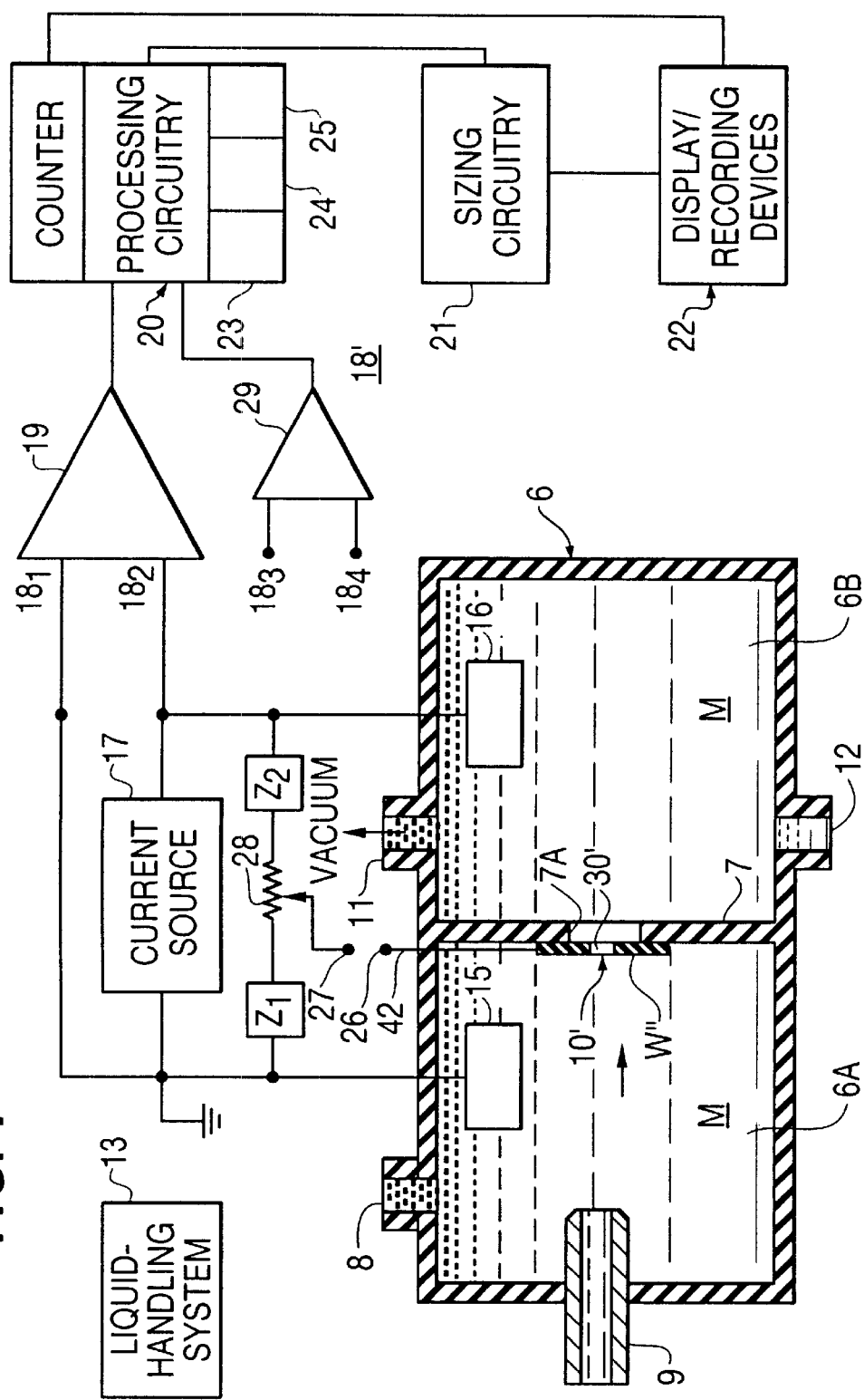
FIG. 7 illustrates a second embodiment of a new apparatus for sensing and characterizing particles; conventional means for controlling temperature of medium M is not indicated.

In FIG. 7 is schematically illustrated, in accordance with a preferred embodiment of the invention, a second form of the new apparatus for sensing and characterizing particles. As in the apparatus of the preceding embodiment, the apparatus of FIG. 7 comprises a dual-compartment dielectric vessel 6 which defines first and second compartments 6A and 6B separated by a dielectric wall 7. Each of said compartments 6A and 6B is adapted to contain, and is filled with, a liquid medium M having electrical impedance per unit volume that differs from that of the particles to be characterized. In general any liquid media (either aqueous or nonaqueous) comprising ionic species may be useful in specific applications of the new apparatus, and those commonly used with Coulter apparatus may find direct application.

A novel particle-sensing structure W", preferably provided as a small independent element (e.g., as a wafer or disc of appropriate dimensions), is sealed over relatively large opening 7A in dielectric wall 7 and is substantially immersed in and surrounded by the liquid medium M filling both compartments of vessel 6. The hydrodynamically smooth wall 30' of a small through-hole transpiercing sensing structure W" defines a particle-sensing conduit 10' which is caused to constitute the only operative fluidic connection between compartments 6A and 6B. The novel structure of sensing structure W" is caused to provide the wall of conduit 10' with a single axisymmetric, delimited region of electrical resistivity substantially less than that of suspending medium M, said conduit wall having electrical resistivity less than or equal to that of medium M over the entire length of said conduit. Sensing structure W" in FIG. 7 is preferably a form of sensing structure W' in FIGS. 3 or 5, but provided with an operative electrical connection 42 as will be discussed in the following Embodiment 4 of the Sensing Structure.

Particles to be sensed and characterized are suspended at an appropriate concentration in a suitable liquid medium, e.g., liquid medium M, and introduced into compartment 6A through a suitable inlet port 8 (or 9) formed therein. A vacuum, provided by an appropriate source in liquid-handling system 13 and operatively coupled to an outlet port 11 suitably formed in compartment 6B, causes the particle suspension to flow from compartment 6A into compartment 6B through conduit 10'. Each particle in the suspension displaces its own volume of liquid medium M, and if the dimensions of conduit 10' and the concentration of particles in the suspension are appropriately selected, particles can be made to transit conduit 10' more or less individually. Excitation electrodes 15 and 16 are positioned in respective compartments 6A and 6B.

Electrodes 15 and 16 are operatively connected to a source 17 of electrical current, whereby a nominal electrical current is caused to flow through conduit 10' simultaneously with the particle suspension. As in the Coulter art, conduit 10' constricts the hydrodynamic field established in liquid medium M, so that wall 30' of conduit 10' surrounds and confines the flow of particle suspension between compartments 6A and 6B. In contrast to the Coulter art, the single axisymmetric, delimited region of lesser electrical resistivity comprised in wall 30' permits a portion of the excitation current to bypass conduit 10' in a functionally advantageous manner.

Current source 17 is preferably a constant-current source, so that the current it supplies is substantially independent of changes in impedance between electrodes 15 and 16 (e.g., due to substitution of conduits 10' having different diameters or lengths, temperature-induced changes in the resistivity of particle-suspending medium M, or substitution of a suspending medium M having a different resistivity). Less preferably, current source 17 may be a voltage source having high internal impedance. Current source 17 may be caused to provide a DC current, an AC current, or a combination of DC and AC currents. Sensing circuitry 18' operates to sense and process pulsations in current between said electrodes occasioned by the passage of particles through conduit 10'.

For differentially monitoring particle-induced impedance changes in the vicinity of sensing structure W", sensing circuitry 18' is provided with an electrical sensing circuit comprised of amplifier 29, impedances $Z_1$ and $Z_2$, and balancing potentiometer 28. In FIG. 7, 26 is the termination of operative electrical connection 42 to sensing structure W", 27 is the electrical termination of the operative slider connection to potentiometer 28, and 183 and 184 are the input terminals to amplifier 29. Preferably, terminals 183 and 184 of amplifier 29 are operatively connected to terminations 26 and 27 whereby amplifier 29 is made responsive to the differential between sensing structure W" and the potential selected by positioning the slider on potentiometer 28. As has been noted, sensing structure W" assumes a potential due to its immersion in medium M, said potential being determined by the impedances formed by the portions of medium M between sensing structure W" and respective electrodes 15 and 16 in vessel 6. The resulting circuit comprising the complex impedances in the two compartments of vessel 6, impedances $Z_1$ and $Z_2$, and balancing potentiometer 28 is a bridge circuit. As is well known in the art of electrical measurement, through selection of respective impedances $Z_1$ and $Z_2$ in the appropriate ratio, the potential of sensing structure W" may be matched to the desired degree by positioning the slider on balancing potentiometer 28. Values of potentiometer 28, $Z_1$, and $Z_2$ may be chosen as is known in said measurement art. It is not required that impedances $Z_1$ and $Z_2$, be discrete electrical components, e.g., either or both may be a suitable volume of medium M, appropriately contained and provided operative electrical contact.

In general, it is preferable that no current pass through electrical connection 42 so that the operative field in the vicinity of sensing structure W" is not affected by the presence of amplifier 29. If the potential of termination 27 is made equal to that of sensing structure W" so that the bridge is balanced, the input impedance of amplifier 29 is not critical, and passage of a particle through conduit 10' will unbalance the bridge to produce a signal pulse. However, if to meet other requirements the bridge is to be operated off-balance, it is preferred that amplifier 29 have high input impedance so that passage of a particle through conduit 10' has only a direct influence on the operative field near sensing structure W". As will be apparent to those skilled in the instrumentation art, balancing of the bridge circuit may be automated through use of a variety of prior-art methods. For example, a digital-to-analog converter responsive to outputs of processing circuitry 20 may be substituted for balancing potentiometer 28.

Sensing circuitry 18' may also be provided with a second sensing circuit 19, operatively connected to excitation electrodes 15 and 16 as in Coulter apparatus. Thus, as individual particles pass through conduit 10', sensing circuit 19 produces an electrical signal pulse having an amplitude, transient response, and/or shape characteristic of the particle's interaction with the operative electric field near and in sensing conduit 10'. It is preferred that sensing circuit 19 be AC-coupled and have low input impedance compared to the conduit impedance.

It is generally preferred that amplifier 19 be operatively connected between excitation electrodes 15 and 16, so that two characterizing signal pulses become available. However, in some applications it may be desirable that said amplifier be connected between termination 26 for sensing structure W" and either electrode 15 or 16, e.g., to better characterize the rising or falling edge, respectively, of a particle pulse or to permit anticipation of the arrival of a particle in the vicinity of conduit 10' as described in aforesaid U.S. Pat. No. 4,161,690. If current flow through electrical connection 42 to sensing structure W" is made to be zero, such determinations may be made with no influence on the operative field in the vicinity of the sensing structure. Thus, in such connections it is preferred that amplifier 19 have a high input impedance.

In some applications it may be desirable to inject current into sensing structure W", e.g., to affect the operative field or to influence ionic effects in its vicinity. This may be achieved by connecting termination 26 directly to termination 27 (if no differential measurement is required) or otherwise by making amplifier 29 an appropriate transimpedance amplifier as known in the Coulter art, its terminals 183 and 184 being connected to terminations 26 and 27. The potential of sensing structure W" then may be placed under influence of the slider on potentiometer 28. Consequently, current can be injected through electrical connection 42, whereby the operative field in the vicinity of sensing structure may be influenced in an advantageous manner, and amplifier 19 may respond to passage of particles through conduit 10'.

Additional circuits 20 process the particle signal pulses from amplifiers 19 and 29 to provide a count of particles exceeding some particular characteristic threshold, i.e., in pulse amplitude or in pulse width at various proportions of pulse amplitude. For the latter, flow rates of less than 5 m/sec are preferred. If liquid-handling system 13 comprises a positive-displacement metering system, e.g., such as disclosed in aforesaid U.S. Pat. No. 2,869,078 such particle counts may be displayed or recorded in terms of particle concentration by appropriate devices 22. Pulse-editing circuitry responsive to artifactual pulses originating in particle coincidence (25) may be desirable. In addition, because the differential signal-to-noise ratios obtainable with apparatus of the present embodiment approximate an order of magnitude improvement over those for APPARATUS EMBODIMENT 1, recursing particles may interfere with the desired analysis and pulse-editing circuitry 24 responsive to artifactual pulses or particle-free sweep flow via inlet 12 may be beneficial.

As has been noted, it is preferred that the apparatus of FIG. 7 comprise at least the two described particle-sensing circuits incorporating respective amplifiers 19 and 29. However, it is neither required that amplifier 19 be present nor that it be connected to both excitation electrodes 15 and 16, e.g., provided appropriate input characteristics and gain, it may be connected between either of said electrodes and termination 26 for sensing structure W".

The aforesaid preferences for APPARATUS EMBODIMENT 1 regarding temperature control-means and appropriate electrodes 15 and 16 apply also to the apparatus of this embodiment and are included herein by reference. In addition, inlet part 8 and flow director 9 may be used to provide control of the conduit electrochemical environment via manipulation of sheath and core flows, as described in APPARATUS EMBODIMENT 1.

Embodiment 4 of the Sensing Structure:

In accordance with the invention, the apparatus of FIG. 7 is characterized by a novel particle-sensing structure W". Sensing structure W" may be any sensing structure W' within the range of the foregoing generic description of such structures, to which is provided an operative electrical connection. It is preferred that said sensing structures be according to the foregoing Embodiment 1 of the Sensing Structure or Embodiment 2 of the Sensing Structure. In FIGS. 8A and 8B are illustrated sensing structures W" derived from those illustrated in respective FIGS. 3 and 5 associated with said embodiments. All requirements therein discussed, including the need for hydrodynamic smoothness of defining wall 30' and preferred L/D ratios for conduit 10', also apply to sensing structures W". As will be appreciated, an electrical connection may be provided to W' in FIGS. 6A and 6B, whereby sensing structure 50 may be substituted for sensing structure W" in FIG. 7. In all embodiments, through said operative electrical connection sensing structure W" functions as an electrode in addition to providing a particle-sensitive region in the electric field established by current flow between electrodes 15 and 16.

In FIGS. 8A and 8B, electrical connection 42 is attached to the conductive material comprised in sensing structures W' with an appropriate electrically conductive joining material 44, and connection 42 and joining material 44 are insulated from medium M by respective electrically insulative materials 43 and 45. Electrical connection 42 and joining material 44 may be any of those forms and materials known to the instrumentation art. For example, electrical connection 42 may a small-gauge insulated (43) wire used for making electrical connections in the electronics art, joined to W' with a compatible conductive metal-filled paste 44. It is preferred that join 44 be located at least several conduit diameters away from conduit 10'. Insulative material 45 may be a dielectric epoxy applied conformally to joining material 44 and the insulation of said wire so as to preclude entry of medium M. To prevent local electrolytic activity due to material differences, it is important that that insulative material 45 extend onto the homogeneous surface of W' and insulative material 43, whereby insulative materials 43 and 45 in combination form a continuous barrier impervious to medium M.

In the apparatus of FIG. 7, sensing structure W" preferably functions both as a novel particle-sensing conduit and as an electrode, to provide a local reference in vessel 6 against which small dynamic impedance changes in the immediate vicinity of the conduit may be determined. In less-preferred forms of the FIG. 7 apparatus, sensing structure W" may be used as a potential-sensing electrode, as when terminals 183 and 184 of amplifier 29 are connected between sensing structure W" and one of the excitation electrodes, 15 or 16. This configuration superficially resembles in some respects one described in aforesaid U.S. Pat. No. 4,161,690. As discussed in connection with Embodiment 3 of the Sensing Structure, according to said patent the particle-sensitive conduit penetrates a three-layer structure comprising a conductive layer in contact with an insulative layer on each major surface; the electrical and fluidic length is the combined thicknesses of the three layers. However, to minimize electrochemical effects the conductive layer serves only as an auxiliary detection electrode and is connected to triggering circuitry functioning to sample the signal pulses sensed between, e.g., electrodes 15 and 16 by amplifier 19 in FIG. 7; it thus does not provide a direct particle-characterization signal. In contrast, sensing structures according to the present invention are used with amplifier 29 to provide a direct determination of a differential particle-characterization signal related to the particle's electrochemical interaction with the local ionic distribution as it approaches or exits the particle-sensing conduit.

Further, in contrast to the volumeter assemblies described in U.S. Pat. No. 4,161,690, sensing structures W" according to FIGS. 8A and 8B consist functionally of a single conductive component, the electrical thickness of which equals length L of conduit 10' so that the electrode comprises the entire functional conduit, i.e., there are no insulative layers. When compared to the prior-art structure, sensing structure W" thus offers commercially important conveniences of manufacture in addition to the novel particle-sensing mechanism.

Features distinguishing sensing structure 50 in FIGS. 6A and 6B from the volumeter assemblies described in U.S. Pat. No. 4,161,690 were discussed in connection with Embodiment 3 of the Sensing Structure. If sensing structures 50 were to be provided an operative electrical connection and substituted for sensing structure W" in FIG. 7, these significant differences would still obtain.

Whereas the value of prior-art apparatus for sensing and characterizing particles by the Coulter principle resides to a large degree in the specificity of particle pulses to particle volume, a major potential of the present invention lies in the responsivity to particle characteristics which may be demonstrable as modifications to the particle pulse originating in electrochemical relations between the particle, the suspending medium, and the material surrounding the conduit through which the suspending medium carries the particle. These advantages arise in the novel properties of new sensing structures, properties which originate in the substantially lesser electrical resistivity (compared to the resistivity of suspending medium M) of an electrically conductive material surrounding at least a portion of the particle-sensing conduit therein. It is believed that the properties of the electrochemical interactions established in the vicinity of such conduits will enable new types of particle-characterizing methods to be developed. While theories are expressed in the foregoing as an aid to explanation, these are not intended to be limiting, irrespective of their degree of correctness.

It is believed that the concepts of the invention are sufficiently described that their significant and distinguishing differences over the prior art may be appreciated. Moreover, it is believed that the embodiments herein described will enable one skilled in the relevant arts to demonstrate practicable apparatus incorporating the concepts of the invention.

In the preceding description, the advance represented by the invention will become apparent to those skilled in the art of particle characterization, and while the invention has been described with reference to particularly preferred embodiments, it will be understood that modifications and enhancements can be made without departing from the spirit and scope of the invention. Similarly, while in the preceding description dielectric particles served to demonstrate the feasibility of volumetrically calibrating apparatus according to the invention, it will be understood that particles of other types, including biological cells or particles composed of conductive materials, may also be sensed and characterized; it is expected that such particle-characterization tasks will require processing circuits or algorithms appropriate to the particular analytic requirement. Such modifications, enhancements, and adaptations to specific particle-characterization applications are intended to be included within the scope of the invention, which scope should be determined with reference to the following claims rather than to the foregoing specification.

What is claimed is:

1. In a particle-sensing apparatus for sensing and characterizing particles suspended in a liquid medium to form a liquid suspension of particles, said apparatus comprising:

(a) a particle-sensing structure having a continuous wall defining a hydrodynamically smooth conduit of predetermined length through which a liquid suspension of particles to be sensed and characterized can be made to pass;

(b) a liquid-handling system effective to cause said liquid suspension of particles to pass through said conduit;

(c) a first electrical circuit effective to produce a nominal electrical current through said conduit, said nominal electrical current being effective to establish in the vicinity of said conduit an electric field providing a particle-sensitive zone in which changes in said nominal electrical current, as produced by particles passing through said conduit simultaneously with said nominal electrical current, are measurable; and (d) a second electrical circuit effective to monitor a characteristic of the nominal electrical current through the conduit to sense characteristics of particles passing through said conduit; the improvement wherein:

said continuous wall is made entirely of an electrically conductive material having electrical resistivity less than or equal to that of the particle-suspending medium, said electrically conductive material being uninsulated over said predetermined length so as to be in operative electrical contact with said liquid particle-suspending medium.

2. The apparatus as defined by claim 1 wherein said continuous wall is operatively coupled to said second electrical circuit.

3. The apparatus as defined by claim 1 wherein said continuous wall is operatively coupled to said first electrical circuit.

4. The apparatus as defined by claim 1 wherein said particle-sensing structure comprises a single wafer of uninsulated electrically conductive material having a small, hydrodynamically smooth through-hole formed therein, said through-hole defining said continuous wall and said the conduit through which the liquid suspension of particles is made to pass.

5. The apparatus as defined by claim 4 wherein said wafer comprises a homogeneous alloy of tungsten or platinum.

6. The apparatus as defined by claim 1 wherein said continuous, conduit-defining wall is defined by a small, hydrodynamically smooth through-hole formed through a plurality of contiguous wafers of uninsulated electrically conductive material, each of said wafers having an electrical resistivity less than or equal to that of said liquid particle-suspending medium, and one of said wafers having a resistivity substantially less than that of the other wafers.

7. The apparatus as defined by claim 6 wherein said particle-sensing structure comprises three contiguous wafers, the center wafer having a resistivity substantially less than that of the other two wafers.

8. The apparatus as defined by claim 1 wherein said particle-sensing structure comprises a single wafer of dielectric material having a small through-hole formed therein, said wafer being clad, in the vicinity of said through hole, with an uninsulated electrically conductive material to define a cladded, hydrodynamically smooth conduit through which said liquid suspension of particles is made to pass.

9. The apparatus as defined by claim 8 wherein said dielectric material comprises ruby, sapphire, silicon dioxide or glass, and wherein said conductive material comprises platinum.

10. Apparatus for sensing and characterizing particles suspended in a liquid medium to form a liquid suspension of particles, said apparatus comprising:
  (a) a hydrodynamically smooth particle-sensing conduit through which said liquid suspension of particles to be sensed and characterized can be made to pass, said particle-sensing conduit being of predetermined length and formed in a solid structure consisting of electrically conductive material having an electrical resistivity substantially less than or equal to the electrical resistivity of said liquid medium, said solid structure being uninsulated over at least said predetermined length so as to be in operative electrical contact with said liquid particle-suspending medium;
  (b) a liquid-handling system effective to cause said liquid suspension of particles to pass through said particle-sensing conduit, said liquid suspension of particles passing through said conduit being in electrical contact with said solid structure throughout said predetermined length;
  (c) a first electrical circuit effective to produce a nominal electrical current through said particle-sensing conduit, said nominal electrical current being effective to establish in the vicinity of said particle-sensing conduit an electric field having a particle-sensitive zone in which changes in said nominal electrical current, as produced by particles passing through said particle-sensing conduit simultaneously with said nominal electrical current, are measurable, said solid structure functioning to establish gradients of ions in the vicinity of said conduit; and
  (d) a second electrical circuit effective to monitor the amplitude of said nominal electrical current through said particle-sensing conduit to sense the characteristics of particles passing through said conduit.

11. For use in a particle-sensing apparatus for sensing and characterizing particles suspended in a liquid medium to form a liquid suspension of particles, said particle-sensing apparatus being of the type comprising: (a) fluidic means effective to cause a liquid suspension of particles to be sensed and characterized to pass through a hydrodynamically smooth particle-sensing conduit of predetermined length; (b) first circuit means effective to cause a nominal electrical current to flow through said conduit simultaneously with said liquid suspension of particles; and (c) second circuit means effective to detect changes in said nominal electrical current as occasioned by the passage of particles through said conduit;
  an electrically conductive particle-sensing structure defining said hydrodynamically smooth particle-sensing conduit, said electrically conductive particle-sensing structure having an electrical resistivity less than or equal to that of said liquid medium, said conduit being formed through said electrically conductive particle-sensing structure and said particle-sensing structure being uninsulated so as to be in operative electrical contact with said liquid particle-suspending medium over said predetermined length of said conduit.

12. The apparatus as defined by claim 11 wherein said particle-sensing structure is provided with an operative electrical connection for coupling to either said first or second circuit means, whereby said particle-sensing structure also functions as an electrode.

13. The apparatus as defined by claim 11 wherein said particle-sensing structure comprises a single wafer of uninsulated electrically conductive material having a small, hydrodynamically smooth through-hole formed therein, said through-hole defining the conduit through which said liquid suspension of particles is made to pass.

14. The apparatus as defined by claim 13 wherein said wafer comprises a homogeneous alloy of tungsten or platinum.

15. The apparatus as defined by claim 11 wherein said particle-sensing structure is a unitary structure comprising a plurality of contiguous wafers of uninsulated electrically conductive material, said wafers each having a small, hydrodynamically smooth through-hole formed therein, said through-holes being fluidically aligned to define the conduit through which said liquid suspension of particles is made to pass, each of said wafers having an electrical resistivity less than or equal to that of the liquid particle-suspending medium, and one of said wafers having a resistivity substantially less than that of the other wafers.

16. The apparatus as defined by claim 15 wherein said particle-sensing structure comprises three contiguous wafers, the center wafer having a resistivity substantially less than that of the other two wafers.

17. The apparatus as defined by claim 11 wherein said particle-sensing structure comprises a single wafer of dielectric material having a small through-hole formed therein, said wafer being clad, in the vicinity of said through hole, with an uninsulated electrically conductive material to define a cladded, hydrodynamically smooth conduit through which said liquid suspension of particles is made to pass.

18. The apparatus as defined by claim 17 wherein said dielectric material comprises ruby, sapphire, silicon dioxide or glass, and wherein said conductive material comprises platinum.

19. A method for sensing and characterizing particles suspended in a liquid medium to form a liquid suspension of particles, said method comprising the steps of:
  (a) causing a liquid suspension of particles to be sensed and characterized to flow through a hydrodynamically smooth conduit formed in a unitary structure;
  (b) producing a nominal electrical current through said conduit while said suspension of particles is passing therethrough, said nominal electrical current being effective to establish throughout said conduit an electric field providing a particle-sensitive zone in which changes in said nominal electrical current, as produced by particles passing through said conduit simultaneously with said nominal electrical current, are measurable, said unitary structure having an electrical resistivity, throughout said conduit, less than or equal to the electrical resistivity of the liquid suspension of particles, and said unitary structure being uninsulated over at least the entire length of said conduit so as to be in operative electrical contact with said liquid medium; and (c) monitoring said nominal electrical current to detect particle-induced changes therein, said changes being characteristic of the properties of particles passing through said conduit.

20. A method for sensing and characterizing particles suspended in a liquid medium to form a liquid suspension of particles, said method comprising the steps of:

(a) providing a particle-sensing structure having a wall defining a hydrodynamically smooth conduit of predetermined length through which a liquid suspension of particles to be sensed and characterized can be made to pass, said wall being electrically conductive and having electrical resistivity less than or equal to that of said liquid medium, said wall being uninsulated so as to be in operative electrical contact with said liquid medium over said predetermined length of said conduit;

(b) causing said liquid suspension of particles to pass through said conduit;

(c) producing a nominal electrical current through said conduit, said nominal electrical current being effective to establish in the vicinity of said conduit an electric field providing a particle-sensitive zone in which changes in said nominal electrical current, as produced by particles passing through said conduit simultaneously with said nominal electrical current, are measurable; and (d) monitoring a characteristic of the nominal electrical current through the conduit to sense characteristics of particles passing through said conduit.

* * * * *

UNITED STATES PATENT AND TRADEMARK OFFICE
CERTIFICATE OF CORRECTION

PATENT NO. : 6,259,242 B1
DATED : July 10, 2001
INVENTOR(S) : Marshall D. Graham and Harvey J. Dunstan It is certified that error appears in the above-identified patent and that said Letters Patent is hereby corrected as shown below:

Column 1,
Line 9, after "to" delete -- application --.

Column 2,
Line 25, change "p" to -- ρ --.

Column 3,
Line 61, after "compartment" insert -- 6B --.
Line 65, change "p" to -- ρ --.

Column 7,
Line 4, change "liquid handling-system" to -- liquid-handling system --.

Column 11,
Line 12, change "an" to -- a --.
Line 58, change "an" to -- a --.

Column 14,
Line 63, after "W" insert a space.

Column 16,
Line 13, after "similar" insert -- to --.

Column 17,
Line 39, after "titanium" insert -- carbide --.

Column 19,
Lines 59-60, after "conduction" delete -- occurs --.

Column 20,
Line 6, after "only" insert -- on --.
Line 33, after "and" change "≠" to -- 16 --.

Column 26,
Line 31, after first "and" change "183 and 184" to -- 18$_3$ and 18$_4$ --.
Line 32, after "terminals" change "183" to -- 18$_3$ --.
Line 33, after "and" change "184" to -- 18$_4$ --.

UNITED STATES PATENT AND TRADEMARK OFFICE
CERTIFICATE OF CORRECTION

PATENT NO. : 6,259,242 B1
DATED : July 10, 2001
INVENTOR(S) : Marshall D. Graham and Harvey J. Dunstan It is certified that error appears in the above-identified patent and that said Letters Patent is hereby corrected as shown below:

Column 27,
Line 38, change "183 and 184" to -- $18_3$ and $18_4$ --.

Column 28,
Line 39, change "W'" to -- W" --.
Line 47, change "W'" to -- W" --.
Line 54, change "W'" to -- W" --.
Line 65, change "183 and 184" to -- $18_3$ and $18_4$ --.

Column 30,
Line 58, after second occurrence of "said" delete "the".

Signed and Sealed this

Seventh Day of May, 2002

*Attest:*

JAMES E. ROGAN
*Attesting Officer*     *Director of the United States Patent and Trademark Office*